United States Patent [19]

Iida et al.

[11] Patent Number: 5,206,349
[45] Date of Patent: Apr. 27, 1993

[54] AROMATIC DIAZO COMPOUNDS AND PHOTOSENSITIVE COMPOSITIONS USING THE SAME

[75] Inventors: Hirotada Iida; Hajime Arai; Hitoshi Sugiura; Katsuhiko Sugou; Kieko Harada, all of Funabashi, Japan

[73] Assignee: Toyo Gosei Kogy Co., Ltd., Chiba, Japan

[21] Appl. No.: 740,636

[22] Filed: Aug. 5, 1991

[30] Foreign Application Priority Data

Aug. 10, 1990 [JP] Japan ................................. 2-210253
Jun. 25, 1991 [JP] Japan ................................. 3-153295

[51] Int. Cl.$^5$ ..................... C07C 245/20; G03C 1/54; G03F 7/016
[52] U.S. Cl. .................................. 534/561; 430/146; 430/157; 430/171; 430/172; 430/175; 430/302; 534/558; 534/560; 534/562; 534/565; 564/443
[58] Field of Search ............. 534/561, 562; 564/443; 430/157, 175, 171, 172, 146, 302

[56] References Cited

U.S. PATENT DOCUMENTS

| | | | |
|---|---|---|---|
| 3,354,209 | 11/1967 | Brack | 564/443 |
| 3,462,492 | 8/1969 | Kober | 564/443 |
| 3,679,419 | 7/1972 | Gillich | 534/561 X |
| 3,790,385 | 2/1974 | Steppan et al. | 534/561 X |
| 4,196,145 | 4/1980 | Halasz et al. | 564/443 X |
| 4,581,313 | 4/1986 | Minamizono et al. | 534/561 X |
| 4,731,316 | 3/1988 | Tomiyastt et al. | 534/561 X |
| 4,902,601 | 2/1990 | Potts et al. | 534/561 X |

FOREIGN PATENT DOCUMENTS

| | | | |
|---|---|---|---|
| 0294669 | 12/1988 | European Pat. Off. | 564/443 |
| 0295474 | 12/1988 | European Pat. Off. | 564/443 |

*Primary Examiner*—Floyd D. Higel
*Attorney, Agent, or Firm*—Bierman and Muserlian

[57] ABSTRACT

An aromatic diazo compound having at least two groups of Formula (I) in the molecule.

This aromatic diazo compound can be handled under visible light free from ultraviolet, is high in photosensitivity, and can be produced by a simple synthesis method.

The diazo compound has a high solubility in organic solvents, appropriate for use as a photosensitive material for a lithographic printing plate, can be easily developed by an alkaline developing solution mainly based on an alkaline aqueous solution, and has a water solubility appropriate for use in a screen printing plate.

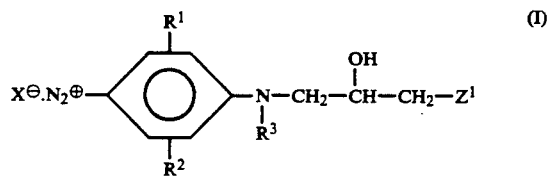

wherein
$Z^1$ indicates

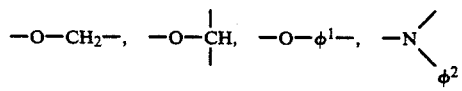

wherein
$\phi^1$ is arylene or substituted arylene; and $-\phi^2$ is $>C=O$, lower alkyl, lower alkylene, or aryl or substituted aryl.
$R^1$ and $R^2$ are H, alkyl of $C_1$ to $C_8$, or alkyloxy of $C_1$ to $C_8$; $X^-$ is anion; and $R^3$ indicates alkyl, saturated alkyl, aralkyl, substituted aralkyl, or a group similar to

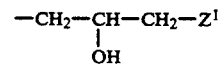

5 Claims, 10 Drawing Sheets

UV absorption spectrum of the diazo compound synthesized in Example 4 and diphenylamine-4-diazonium salt/formaldehyde condensate ——— Example 4(Diazo compound(10))

········ Diphenylamine-4-diazonium salt/formaldehyde condensate synthesized in Comparative Exam. 1

$^1$H NMR (270 MHz acetone-d$_6$, TMS) spectrum of a compound of Formula (69).

$^1$H NMR (270 MHz ACETONE-$d_6$, TMS) SPECTRUM OF A COMPOUND OF FORMULA (71).

$PF_6 \cdot N_2\text{—}\langle O \rangle\text{—}N(C_2H_5)_2$

Ultraviolet absorption spectra of diazo compounds of Formulas (69), (71), and (73).

AROMATIC DIAZO COMPOUNDS AND PHOTOSENSITIVE COMPOSITIONS USING THE SAME

FIELD OF THE INVENTION

This invention relates to novel photosensitive aromatic diazo compounds, which are high in photosensitivity, have a good storage stability, and are easy to be synthesized, a production method thereof, and photosensitive compositions using the same.

BACKGROUND OF THE INVENTION

Heretofore, as a typical photosensitive substance to be mixed in photosensitive coating layers of photosensitive lithographic printing plate and photosensitive screen printing plate, a condensate (so-called diazo resin) of diphenylamine-4-diazonium salt (or 4-phenylamino-benzenediazonium salt) and formaldehyde has been used. Production methods for such a multifunctional diazo condensate are described in specifications of U.S. Pat. Nos. 2,679,498, 2,922,715, 2,946,683, 3,050,502, 3,311,605, 3,163,633, 3,406,159, and 3,277,074. These diazo condensates, although having many advantageous properties as practical photosensitive substances, have problems which have yet to be solved.

A first problem is that these diazo condensates are relatively less soluble in organic solvents. This is especially true when inorganic ions such as halide ions or phosphate ion are used as counterions to the diazonium group of these diazo compounds, and, when sulfonate ions such as benzenesulfonic acid, toluenesulfonic acid, or an alkylsulfonic acid are used, their solubility is insufficient in such organic solvents as glycol ethers, alcohols, ketones and the like. Such low solubility in organic solvents is a problem with these diazo condensates when used as photosensitive agents in photosensitive lithographic printing plates.

Various investigations have been attempted to solve such a problem. For example, Japanese Patent Publication 53-24449/1978 discloses the use of a special compound such as 2-hydroxy-4-methoxybenzophenone-5-sulfonic acid as a counterion to the diazonium group, which enhances the solubility in organic solvents.

Japanese Patent Publication 49-45323/1974 discloses the use of a special compound such as 4,4'-bismethoxymethyldiphenylether as a condensation agent for diphenylamine-4-diazonium salt in place of formaldehyde, which provides the same improvement. Furthermore, Japanese Patent Publication Laid-open 2-3049/1990 discloses the use of hexamethoxymethyl-melamine as a special condensation agent.

A second problem is that, since diazo condensate using diphenylamine-4-diazonium salt as a basic structural unit has an absorption in the visible light region at 420–500 nm, it tends to absorb light of this wavelength and decompose, and is thus difficult to be handled under visible light free from ultraviolet, which constitutes a disadvantage for production and use.

As a method which simultaneously solves the second and first problems, there has been investigated a novel multifunctional diazo compound which basically differs in chemical structure from that of prior art diazo compounds. The thus obtained novel diazo compound comprises 4-dialkylaminobenzene-diazonium salt as a basic structural unit, in place of the conventional diphenylamine-4-diazonium salt.

For example, Japanese Patent Publication Laid-open 54-30121/1979 and Japanese Patent Publication Laid-open 61-273538/1986 use two or more 4-dialkylaminobenzene-diazonium salts, which are ester bonded to form a multifunctional diazonium salt. Further, Japanese Patent Publication 157332/1989 uses 4-dialkylaminobenzene-diazonium salt, which is bonded in the form of a polyalkylamine to form a multifunctional diazonium salt. However, although these novel types of diazo compounds have advantageous properties, their production is generally not easy. Furthermore, diazo compounds which are made multifunctional by ester bonding in the above laid-open Japanese Patent Publications have a problem in that the ester bond tends to be hydrolyzed.

A third problem is that diazo compounds used for photosensitive screen printing plates are essentially required to have a high solubility in water. In this respect, no diazo compounds have been reported which have the performance over the prior art diazo compounds comprising diphenylamine-4-diazonium salt condensed with formaldehyde. In Japanese Patent Publication Laid-open 2-11198/1990, diphenylamine-4-diazonium salt is condensed with formaldehyde to obtain highly water-soluble multifunctional diazo compounds. However, these compounds have been developed to improve the developability of the lithographic printing plate after exposure with an alkaline aqueous solution, but do not provide an improvement for screen printing.

A fourth problem is that currently used condensates of diphenylamine-4-diazonium salt with formaldehyde are insufficient in photosensitivity. Therefore, photosensitive compositions using the current multifunctional diazo compounds as photosensitive agents are difficult to shorten the practical exposure time, and, when the exposure time is reduced, the image after development tends to be colored in brown.

As described above, the prior art compounds have problems which have yet to be solved. Including a primary object of the present invention, these problems are summarized as follows:

1) Development of a multifunctional diazo compound which can be handled under visible light free from ultraviolet.

2) Development of a multifunctional diazo compound which, as a photosensitive agent for a lithographic printing plate, is high in solubility in appropriate organic solvents, and is easy to be developed with a developing solution mainly comprising an alkaline aqueous solution.

3) Development of a multifunctional diazo compound which is suitable as a photosensitive agent for screen printing plate.

4) Development of a multifunctional diazo compound which is high in photosensitivity.

5) Development of a multifunctional diazo compound which is easy to be synthesized, and establishment of a low-cost production method for the compound.

6) Development of a photosensitive composition which effectively utilizes the properties of the thus obtained novel multifunctional diazo compound(s).

SUMMARY OF THE INVENTION

The inventors have conducted intensive studies and found a novel aromatic diazo compound which is ideally suitable to attain the above objects 1) to 6), and achieved the present invention. In accordance with the present invention, based on the above findings, there is provided an aromatic diazo compound mainly comprising a compound having at least two groups of Formula (I) in the molecule:

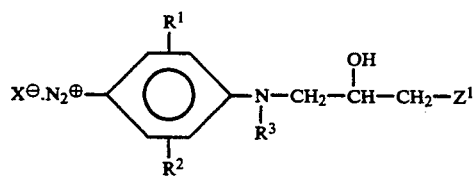

wherein $Z^1$ indicates the following Formula (A); $R^1$ and $R^2$ are H, alkyl or alkyloxy of 1 to 8 carbon atoms; $X^-$ is anion; and $R^3$ indicates the following Formula (B).

Formula (A)

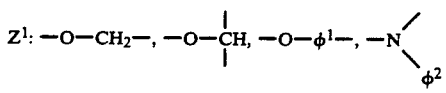

wherein $\phi^1$ is arylene or substituted arylene having no reactivity to diazonium salt or nitrous acid; $-\phi^2$ is $>C=O$, lower alkyl, lower alkylene, or aryl or substituted aryl having no reactivity to diazonium salt or nitrous acid and having no diazo group.

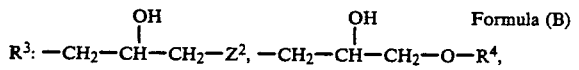

alkyl, saturated alkyl, aralkyl, or substituted aralkyl having no reactivity to diazonium salt or nitrous acid. Wherein, $Z^2$ is $-O-CH_2-$,

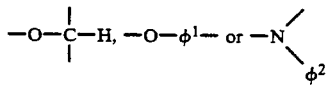

($\phi^2$ indicates means the same as that for Formula (A)), same as or different from $Z^1$; $R^4$ is alkyl of $C_1$ to $C_8$, substituted alkyl, aryl, or substituted aryl having no reactivity to diazonium salt or nitrous acid.

$X^-$ in Formula (I) includes as follows: $Cl^-$, $Br^-$, $\frac{1}{2}SO_4^{2-}$, $H_2PO_4^-$, $\frac{1}{2}HPO_4^{2-}$, $HSO_3^-$, $\frac{1}{2}ZnCl_2Cl^-$, $\frac{1}{2}ZnCl_2Br^-$, $BF_4^-$, $PF_6^-$, benzenesulfonate anion, toluenesulfonate anion, dodecylbenzenesulfonate anion, mesitylenesulfonate anion, naphthalenesulfonate anion, naphthalenedisulfonate anion, 2-hydroxy-4-methoxybenzophenone-5-sulfonate anion, or methanesulfonate anion.

Preferable examples of $Z^1$ in Formula (I) are:

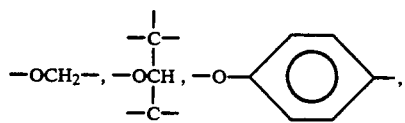

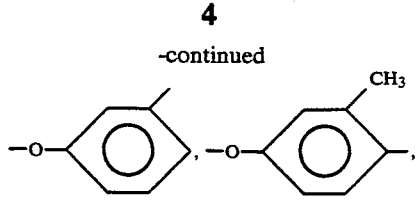

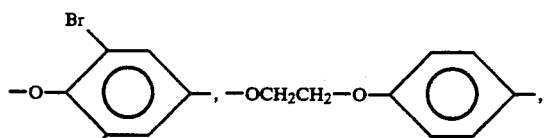

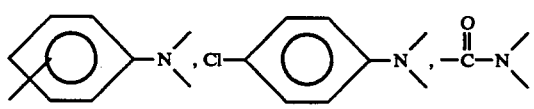

Preferable examples of $R^3$ in Formula (I) are shown in Formulas (D) and (E).

Formula (D)

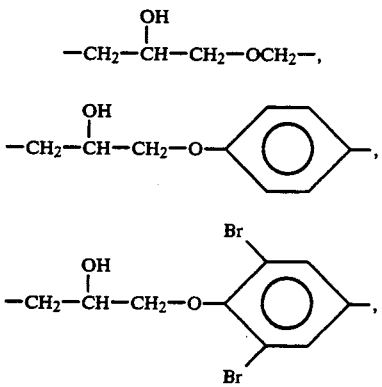

Formula (E)

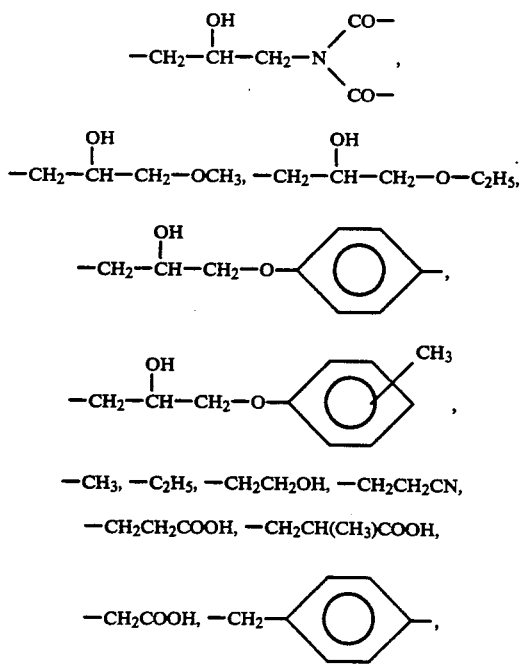

-continued

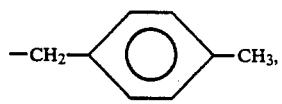

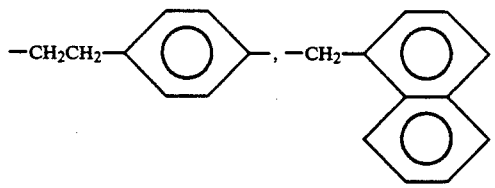

Typical examples of aromatic diazo compounds (aromatic diazo compounds of first to fifth types) having two or more groups of Formula (I) are shown below:

Aromatic diazo compounds of a first type are those of Formula (II).

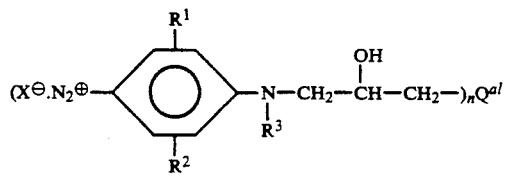 (II)

wherein n=2 to 20; $Q^{al}$ is an aliphatic or aromatic polyol, with n units of H of OH groups removed, of which typical examples are shown in Formulae a) to k); $R^1$ and $R^2$ are H, alkyl or alkyloxy of 1 to 8 carbon atoms; $X^-$ is anion; $R^3$ is alkyl, substituted alkyl, aralkyl, substituted aralkyl, or

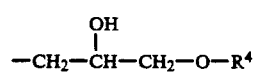

wherein $R^4$ is alkyl, substituted alkyl, aryl, or substituted aryl.

 a)

wherein m is an integer from 0 to 8; and EMG denotes the following group:

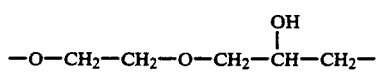

-continued

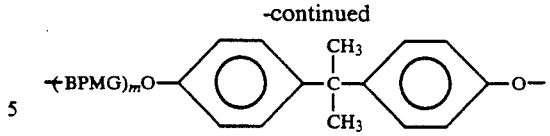 b)

wherein m is an integer from 0 to 4; and BPMG denotes the following group:

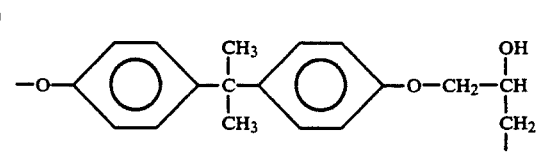

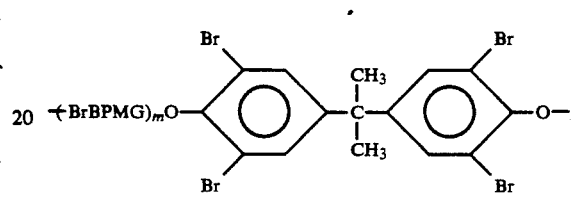 c)

wherein m is an integer from 0 to 3; and BrBPMG denotes the following group:

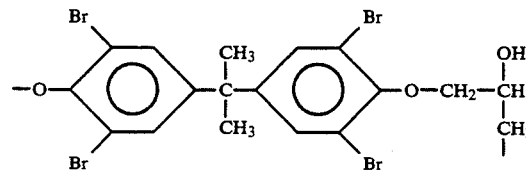

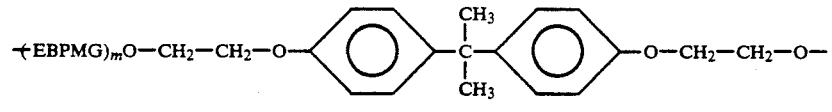 d)

wherein m is an integer from 0 to 4; and EBPM denotes the following group:

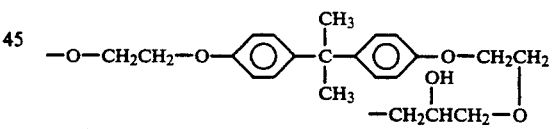

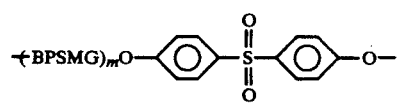 e)

wherein m is an integer from 0 to 3; and BPSMG denotes the following group:

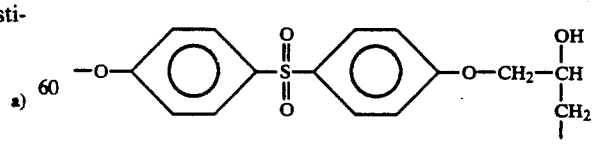

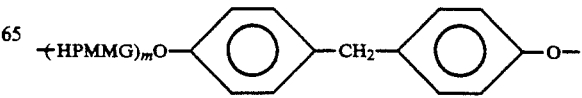 f)

wherein m is an integer from 0 to 4; and HPMMG denotes the following group:

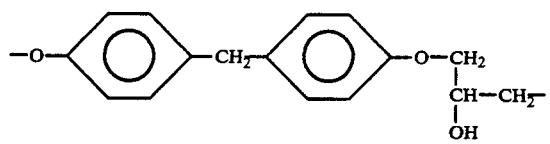

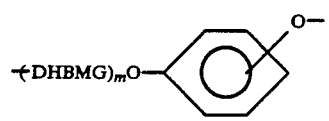 g)

wherein m is an integer from 0 to 3; and DHBMG denotes the following group:

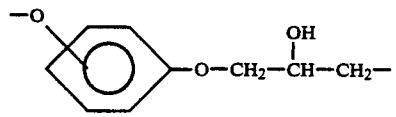

h) $C_3H_5[(OH)_3-nH]$
wherein $C_3H_5(OH)_3$ denotes a glycerine molecule; and m is 2 or 3.

i) $C_5H_8[(OH)_4-nH]$
wherein $C_5H_8(OH)_4$ denotes a pentaerythritol molecule; and n is 2, 3, 4, or 5.

j) $C_6H_8[(OH)_6-nH]$
wherein $C_6H_8(OH)_4$ denotes a sorbitol molecule; and n is 3, 4, 5, or 6.

k) $PXFR[(OH)_m-nH]$
wherein $PXFR(OH)_m$ denotes a phenol- or cresol-formaldehyde condensate; m is 5 to 15; and n is 3 to 10.

Aromatic diazo compounds of a second type are those of Formula (III).

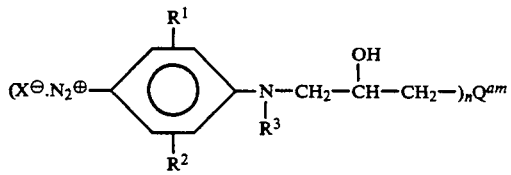

wherein n=2 to 20; $Q^{am}$ is an amino compound radical, with n units of H removed from $-NH_2$ or $=NH$, of which typical formulas are shown in Formulae l) to q); $R^1$ and $R^2$ are H, alkyl of 1 to 8 carbon atoms or alkyloxy of 1 to 6 carbon atoms; $X^-$ is anion; $R^3$ is alkyl, substituted alkyl, aralkyl, substituted aralkyl, or

wherein $R^4$ is alkyl, substituted alkyl, aryl, or substituted aryl.

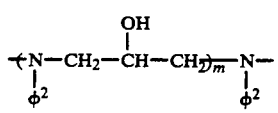 l)

wherein $\phi^2$ is

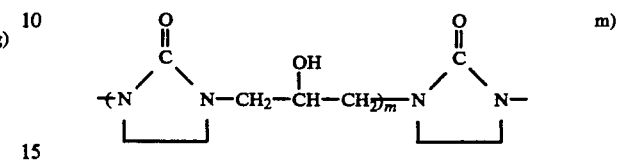

or alkyl of $C_1$ to $C_8$; and m is an integer from 0 to 4.

m)

wherein m is an integer from 0 to 4.

n)

o)

p)

q)

m=2 to 10

Aromatic diazo compounds of a third type are long chain molecules, those of Formula (IV) shown below:

(IV)

wherein n is 2 to 20; $Q_2$ is a divalent group of aliphatic or aromatic diol, with two units of H removed from two OH groups, or an amino compound, with two units of H removed from those attached to N, of which chemical formulas are respectively a) to g) of Formula (II) and l) and m) of Formula (III); $R^1$ and $R^2$ are alkyl or alkoxy of 1 to 8 carbon atoms; $R^5$ denotes Formula (F); and $R^6$ denotes Formula (G).

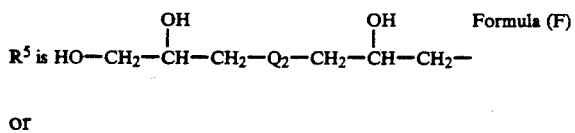

Formula (F)

or

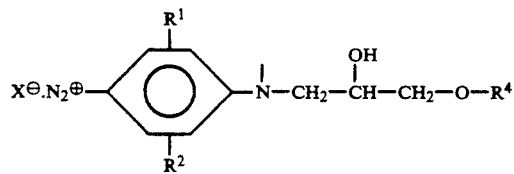

wherein $R^4$ is alkyl, substituted alkyl, aryl, or substituted aryl.

Formula (G)
$R^6$ is —OH or

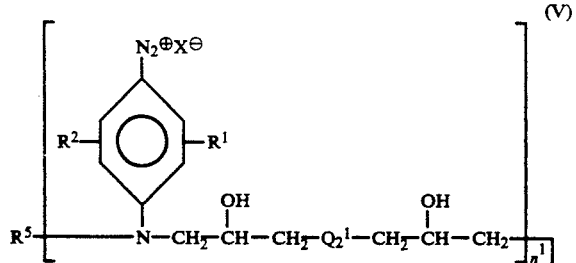

wherein $R^1$ and $R^2$ are alkyl of $C_1$ to $C_8$ or alkyloxy of $C_1$ to $C_8$.

Aromatic diazo compounds of a fourth type are long chain molecules similar to those of the third type. However, the groups connecting the benzenediazoniums are not uniform, but are two or more different types, as aromatic diazo compounds of Formula (V).

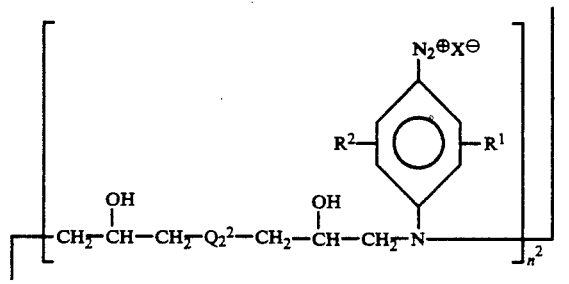

(V)

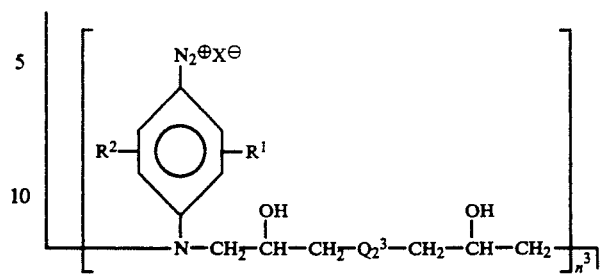

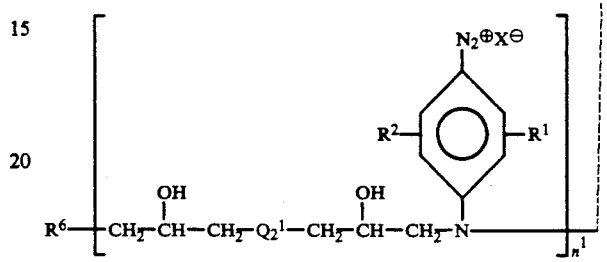

wherein n to $n^i$ are individually an integer from 0 to 4; $n^1 + n^2 + n^3 + \ldots + n^i = 2$ to 20; $X^-$, $R^5$, and $R^6$ are the same as in Formula (IV); and $Q_2{}^1$ to $Q_2{}^i$ are divalent groups belonging to $Q_2$ in Formula (IV), and $Q_2{}^1$ to $Q_2{}^i$ are not the same groups, but are groups of at least two different types.

Aromatic diazo compounds of a fifth type are those having two or more groups of Formula (I) and at least one group of Formula (VI) in the molecule.

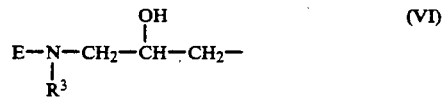

(VI)

wherein E denotes alkyl, substituted alkyl, aryl, substituted aryl, aralkyl, or substituted aralkyl; $R_3$ is the same as that in Formulae (II) and (III).

The aromatic diazo compounds of the fifth type are represented as derivatives of the aromatic diazo compounds of the first to fourth types, as Formulae (II'), (III'), and (V').

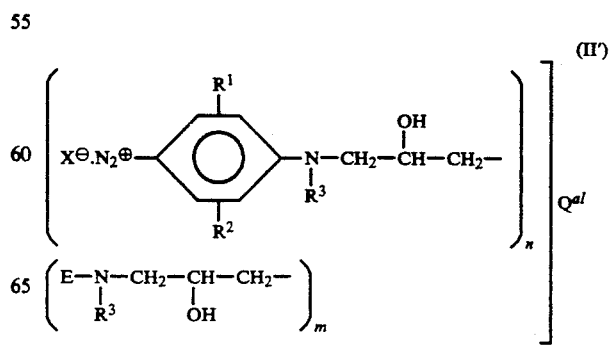

(II')

-continued

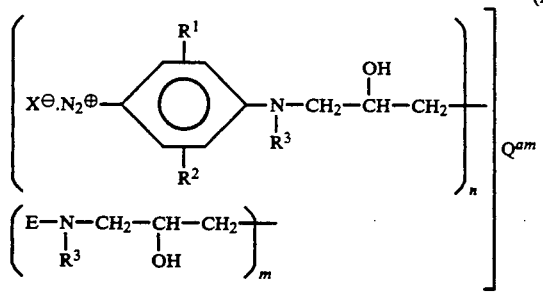

wherein $X^-$, $R^1$, $R^2$, $R^3$, $Q^{al}$, and $Q^{am}$ are the same as those in Formulas (II) and (III); n is 3 to 20; and m is 1 to 10.

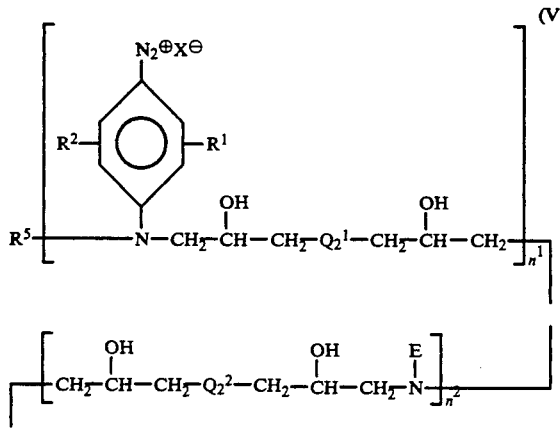

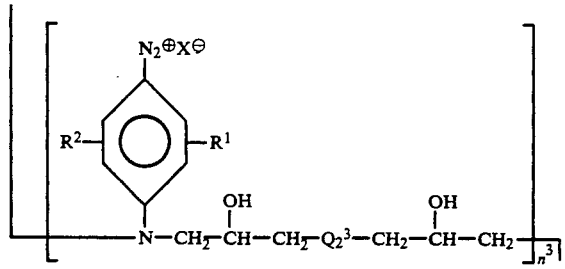

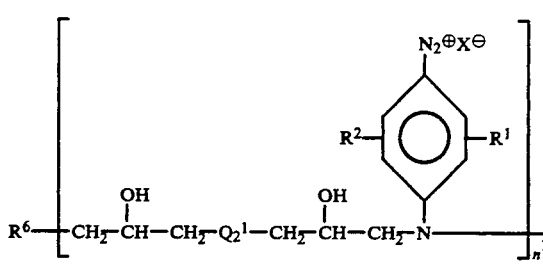

wherein n to $n^i$, $X^-$, $R^5$, and $R^6$ are the same as those in Formula (IV); and $Q_2^1$ to $Q_2^i$ are divalent groups belonging to $Q_2$ in Formula (IV) of the same or two or more different types.

In Formulae (II'), (III'), and (V'), E denotes alkyl, substituted alkyl, aryl, substituted aryl, aralkyl, or substituted aralkyl, of which typical ones are as follows:
Alkyl of 1 to 20 carbon atoms.
Halogen, hydroxyl, carboxyl, or sulfonamide-substituted alkyl of 1 to 20 carbon atoms.
Phenyl, naphthyl, or its alkyl substitution.
Halogen, carboxyl, or sulfonamide-substituted aryl.
Aralkyl having benzyl or aryl substituted with carboxyl or sulfonamide.

Production methods (I) to (IX) of the aromatic diazo compound according to the present invention will now be described.

As a first embodiment of the production method (production method (I) of the aromatic diazo compound according to the present invention, p-aminoacylanilide of Formula (VII) or its substitution and polyglycidylether of Formula (VIII) are reacted in an organic solvent, and, when $R^7$ of Formula (VII) is hydrogen, which is remained after the reaction, the residual hydrogen is substituted with $R^3$, to obtain a compound of formula ($II_{AC}$).

The compound is then reacted with sulfuric acid, hydrochloric acid, or phosphoric acid, or mixtures thereof to substitute the acyl ($A_c$) as a protective group for the amino group with hydrogen to obtain an aromatic amino compound of Formula ($II_a$).

The aromatic amino compound is diazotized with a diazotization reagent such as nitrous acid to obtain the aromatic diazo compound of the first type.

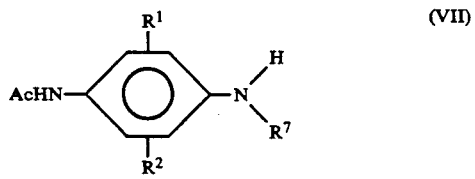

wherein $A_c$ denotes an amino protective group of acyl such as acetyl, propionyl, or benzoyl, or arylsulfonyl; $R^1$ and $R^2$ are the same as those in Formula (II); and $R^7$ is hydrogen or the same as $R^3$ in Formula (II).

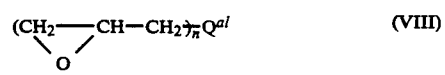

wherein $Q^{al}$ and n are the same as those in Formula (II).

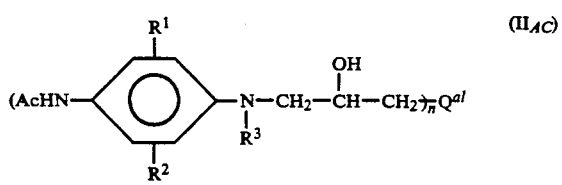

wherein $Q^{al}$, $R^1$, $R^2$, $R^3$, and n are the same as those in Formula (II).

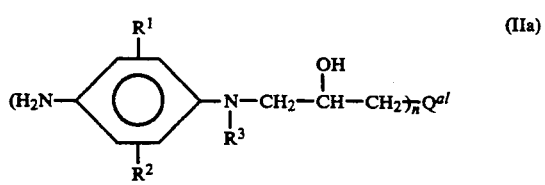

wherein $Q^{al}$, $R^1$, $R^2$, $R^3$, and n are the same as those in Formula (II).

As a second embodiment of the production method (production method (II)) of the aromatic diazo compound according to the present invention, p- aminoacylanilide of Formula (VII) or its substitution product and polyglycidylamino compound of Formula (IX) are reacted in an organic solvent, when $R^7$ of Formula (VII) is hydrogen, which is remained after the reaction, the residual hydrogen is substituted with $R^3$, to obtain a compound of Formula (III$_{AC}$).

The compound is then reacted with sulfuric acid, hydrochloric acid, or phosphoric acid, or mixtures thereof to substitute the acyl (A$_c$) as a protective group for the amino group with hydrogen to obtain an aromatic amino compound of Formula (III$_a$).

The aromatic amino compound is diazotized with a diazotization reagent to obtain the aromatic diazo compound of the second type.

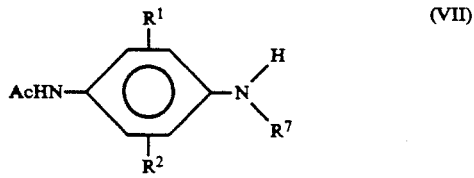
(VII)

wherein Ac denotes an amino protective group of acryl such as acetyl, propionyl, or benzoyl, or arylsulfonyl; $R^1$ and $R^2$ are the same as those in Formula (II); and $R^7$ is hydrogen or same as $R^3$ in Formula (II).

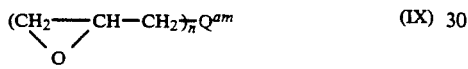
(IX)

wherein $Q^{am}$ and n are the same as those in Formula (III).

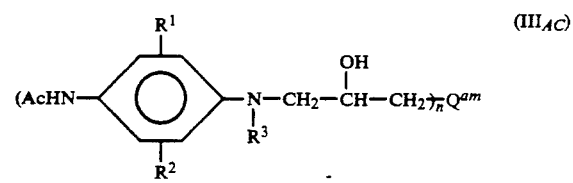
(III$_{AC}$)

wherein $Q^{am}$, $R^1$, $R^2$, $R^3$, and n are the same as those in Formula (III).

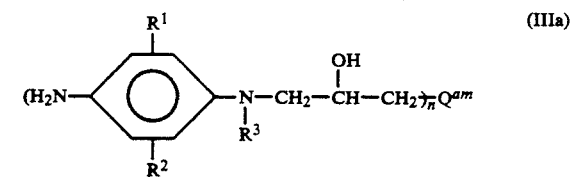
(IIIa)

wherein $Q^{am}$, $R^1$, $R^2$, $R^3$, and n are the same as those in Formula (III).

As a third embodiment of the production method (production method (III)) of the aromatic diazo compound according to the present invention, aniline or its homologue of Formula (X) and a polyglycidylether of Formula (VIII) are reacted in an organic solvent, when $R^7$ of Formula (X) is hydrogen, which is remained after the reaction, the residual hydrogen is substituted with $R^3$, and then reacted with a nitrosating agent to obtain an aromatic nitroso compound of Formula (II$_{NO}$).

The nitroso group is then reduced into amino group to obtain an aromatic amino compound of Formula (II$_a$), which is diazotized to yield the aromatic diazo compound of the first type.

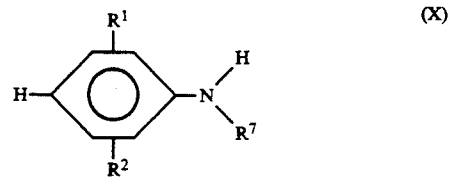
(X)

wherein $R^1$, $R^2$, and $R^7$ are the same as those in Formulas (VII).

(CH$_2$——CH—CH$_2$)$_n$Q$^{al}$  (VIII)
\\ O / wherein $Q^{al}$ and n are the same as those in Formulas (II).

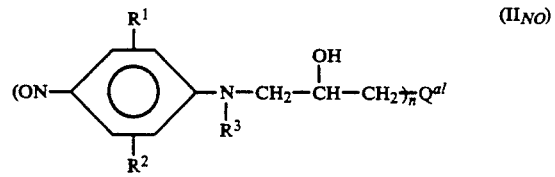
(II$_{NO}$)

wherein $Q^{al}$, $R^1$, $R^2$, $R^3$, and n are the same as those in Formula (II).

As a fourth embodiment of the production method (production method (IV)) of the aromatic diazo compound according to the present invention, aniline or its homologue of Formula (X) and a polyglycidyl amino compound of Formula (IX) are reacted in an organic solvent, when $R^7$ of Formula (X) is hydrogen, which is remained after the reaction, the residual hydrogen is substituted with $R^3$, and then reacted with a nitrosating agent to obtain an aromatic nitroso compound of Formula (III$_{NO}$).

The nitroso group is then reduced into amino group to obtain an aromatic amino compound of Formula (III$_a$), which is diazotized to yield the aromatic diazo compound of the second type.

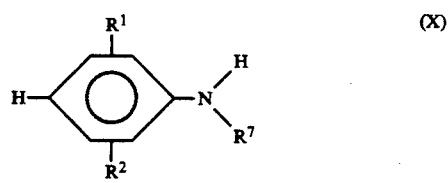
(X)

wherein $R^1$, $R^2$, and $R^7$ are the same as those in Formula (VII).

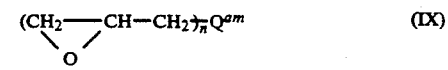
(IX)

wherein $Q^{am}$ and n are the same as those in Formula (III).

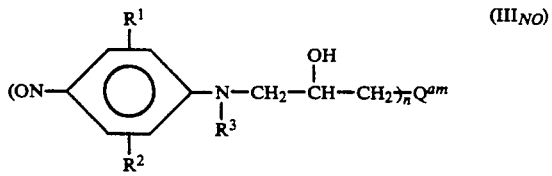

wherein $R^1$, $R^2$, and $R^7$ are the same as those in Formula (III).

As a fifth embodiment of the production method (production method (V)) of the aromatic diazo compound according to the present invention, p-aminoacylanilide of Formula (XI) or its substitution product and a diglycidylether of Formula $(VIII_{n=2})$ or a diglycidylamino compound of Formula $(IX_{n=2})$ are reacted in an organic solvent, when hydrogen atom of the $-NH_2$ group of Formula (XI) is remained after the reaction, reacted with monoglycidylether of Formula (XII), $A_c$ is substituted with H by the same reaction as in the production method (II), and then diazotized to yield the aromatic diazo compound of the third type, which is a long chain molecule.

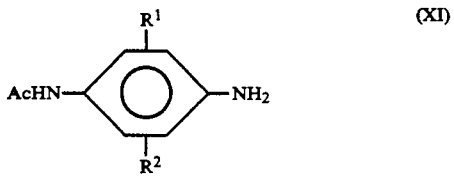

wherein $A_c$, $R^1$, and $R^2$ are the same as those in Formula (VII).

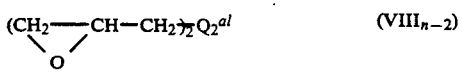

wherein $Q_2^{al}$ is a divalent group belonging to $Q^{al}$ of Formula (II).

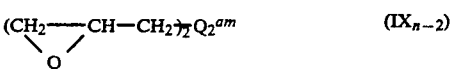

wherein $Q_2^{am}$ is a divalent group belonging to $Q^{am}$ of Formula (III).

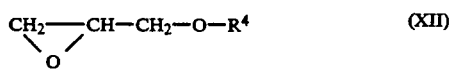

wherein $R^4$ is the same as that in Formula (I).

As a sixth embodiment of the production method (production method (VI)) of the aromatic diazo compound according to the present invention, p-aminoacylanilide of Formula (XI) or its substitution product and a mixture of at least two of diglycidylether of Formula $(VIII_{n=2})$ and diglycidylamino compound of Formula $(IX_{n=2})$ are reacted in an organic solvent, when hydrogen atom of $-NH_2$ of Formula (XI) is remained after the reaction, further reacted with monoglycidylether of Formula (XII), $A_c$ is substituted with H by the same reaction as in the production method (II), and then diazotized to yield the aromatic diazo compound of the fourth type, which is a long chain molecule.

As a seventh embodiment of the production method (production method (VII)) of the aromatic diazo compound according to the present invention, a compound, which has at least one group of Formula (I) in the molecule and is capable of reacting with a carbonyl reagent such as formaldehyde to yield a condensation polymer, is reacted with formaldehyde or a formaldehyde-evolving reagent in sulfuric acid or phosphoric acid.

As an eighth embodiment of the production method (production method (VIII)) of the aromatic diazo compound according to the present invention, a compound, which has at least one group of Formula $(II_{AC})$ in the molecule and is capable of reacting with a carbonyl reagent such as formaldehyde to yield a condensation polymer, is reacted with a carbonyl-evolving reagent such as formaldehyde in an acidic solvent to obtain a compound having at least one group of Formula $(II_{AC})$ in the molecule, which is then deacylated and diazotized.

As a ninth embodiment of the production method (production method (IX)) of the aromatic diazo compound according to the present invention, p-aminoacetanilide of Formula (XI) or its substitution product and an amino compound of Formula (XIII) are mixed in a desired ratio, reacted with a glycidyl compound using the same procedure as in the production methods (I), (II), (V), and (VI), reacted with a strong acid aqueous solution to substitute the acyl amino protective group ($A_c$) with H, and then diazotized.

wherein $R^3$ denotes hydrogen, alkyl, substituted alkyl, aralkyl, or substituted aralkyl; E denotes alkyl, substituted alkyl, aryl, substituted aryl, aralkyl, or substituted aralkyl.

There is also provided according to the present invention a photosensitive composition comprising an aromatic diazo compound mainly comprising a compound having two or more groups of Formula (I) in the molecule and a binder, and, as needed, auxiliaries such as a coloring material or a stabilizer.

The present invention will now be described in detail.

Compounds of Formulae (1) to (24), which are respectively main ingredients of the novel aromatic diazo compound according to the present invention, but are not limited to, are shown below:

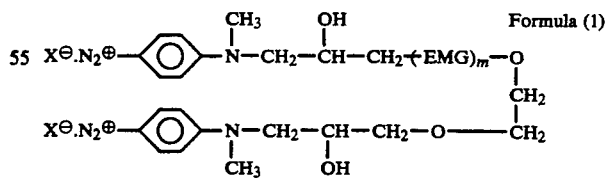

wherein EMG denotes

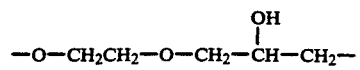

and m is an integer from 0 to 8.

Formula (2)

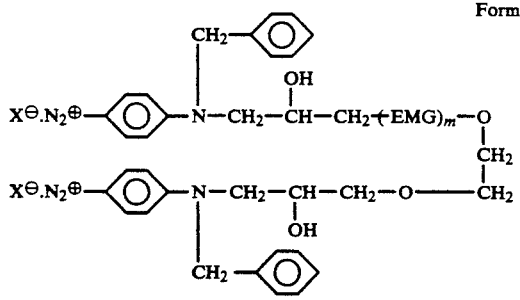

wherein EMG and m are the same as those in Formula (1).

Formula (3)

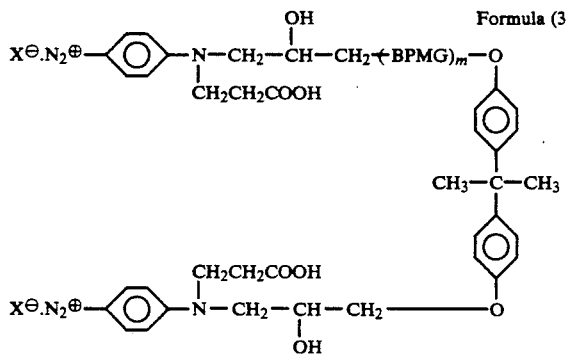

wherein BPMG denotes

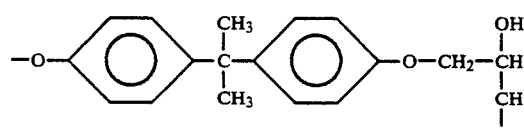

and m is an integer from 0 to 4.

Formula (4)

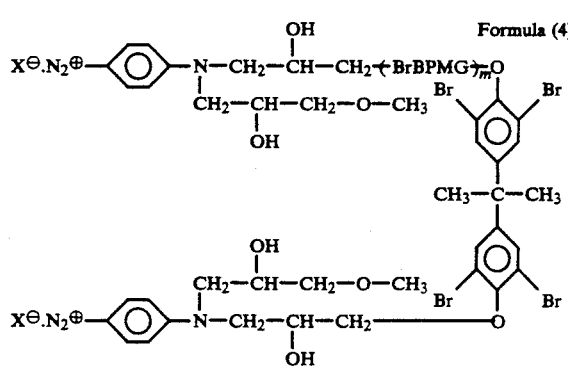

wherein BrBPMG denotes

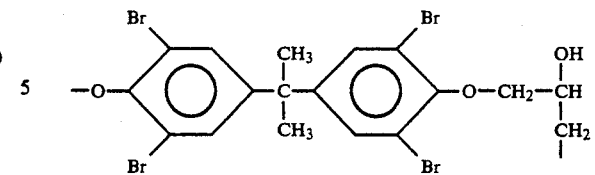

and m is an integer from 0 to 4.

Formula (5)

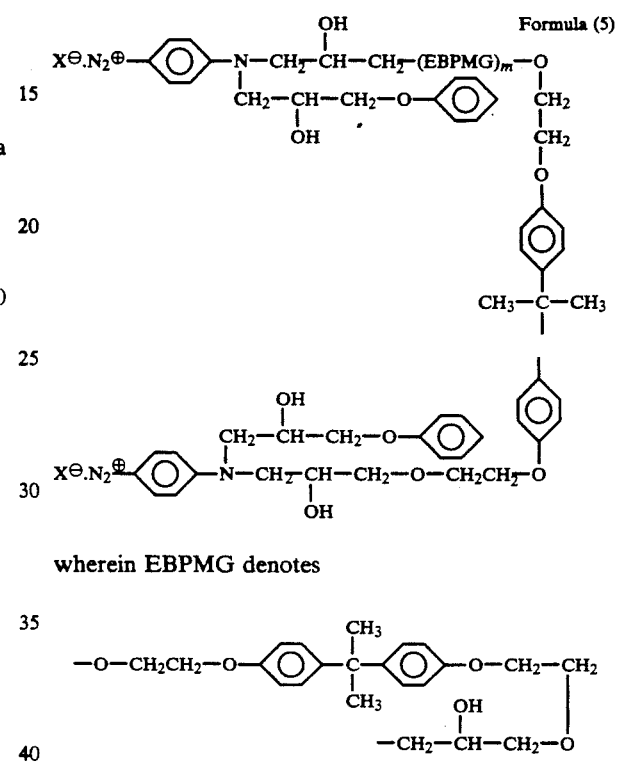

wherein EBPMG denotes

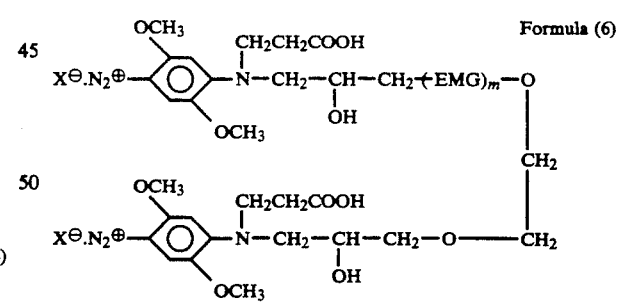

and m is an integer from 0 to 4.

Formula (6)

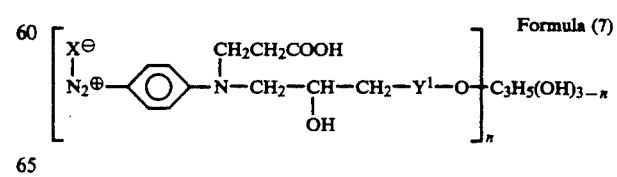

wherein EMG and m are the same as those in Formula (1).

Formula (7)

$$\left[ \begin{array}{c} X^{\ominus} \\ N_2^{\oplus} \end{array} \!\!-\!\!\bigcirc\!\!-\!\!N\!\!-\!\!CH_2\!\!-\!\!CH\!\!-\!\!CH_2\!\!-\!\!Y^1\!\!-\!\!O \right]_n \!\!\!\!-\!\! C_3H_5(OH)_{3-n}$$

wherein n is 2 or 3; $C_3H_5(OH)_3$ denotes glycerine; $Y^1$ is a bond or denotes a divalent group derived from a lower condensate of epichlorohydrin and glycerine.

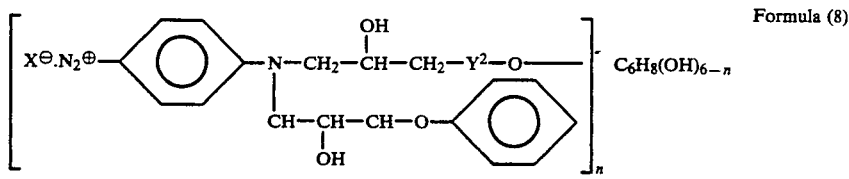

Formula (8)

wherein n is an integer from 3 to 6; $C_6H_8(OH)_6$ denotes sorbitol; $Y^2$ does not exist or denotes a divalent group derived from a lower condensate of epichlorohydrin and sorbitol.

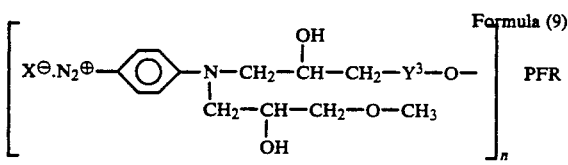

Formula (9)

wherein n is an integer from 2 to 10; PFR denotes a group of phenol-formaldehyde condensate molecule, with n units of phenolic OH removed; $Y^3$ does not exist or denotes a divalent group derived from a lower condensate of epichlorohydrin and phenol-formaldehyde condensate molecule.

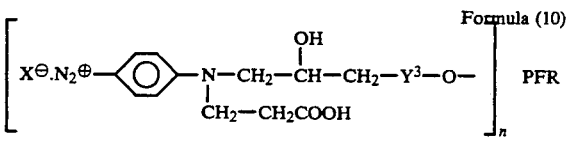

Formula (10)

wherein n, PFR, and $Y^3$ are the same as those in Formula (9).

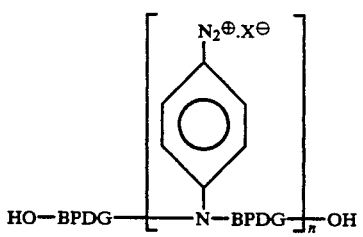

Formula (11)

wherein n is an integer from 2 to 10; and BPDG denotes the following group:

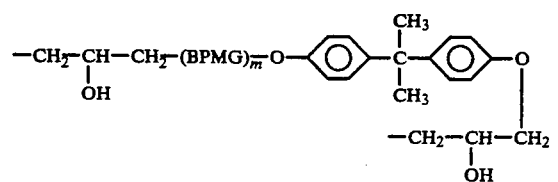

wherein BPMG and m are the same as those in Formula (3).

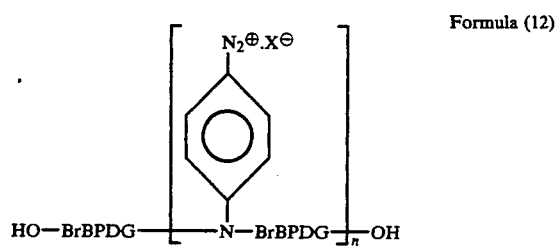

Formula (12)

wherein n is an integer from 2 to 8; and BrBPDG denotes the following group:

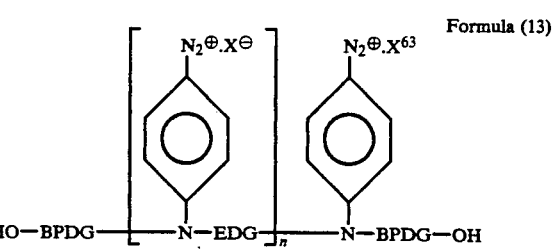

wherein BrBPMG and m are the same as those in Formula (4).

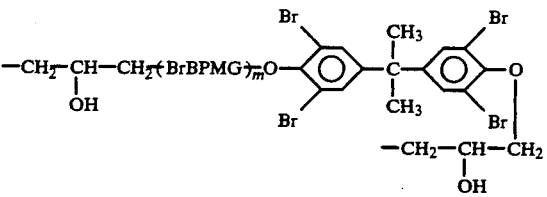

Formula (13)

wherein n and BPDG are the same as those in Formula (11); and EDG denotes the following group:

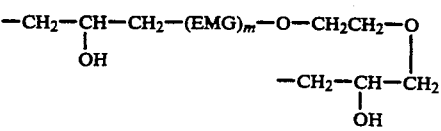

wherein EMG in Formula (EDG) and m are the same as those in Formula (1).

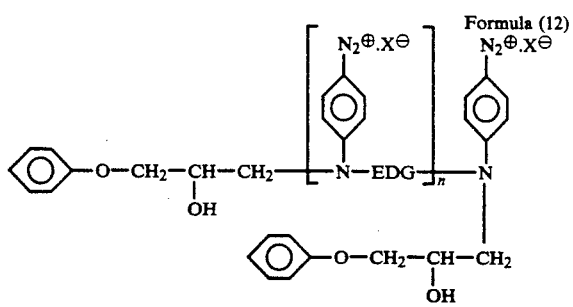

Formula (12)

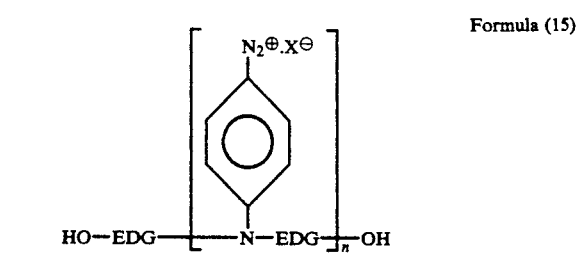

Formula (15)

wherein n and EDG are the same as those in Formula (13).

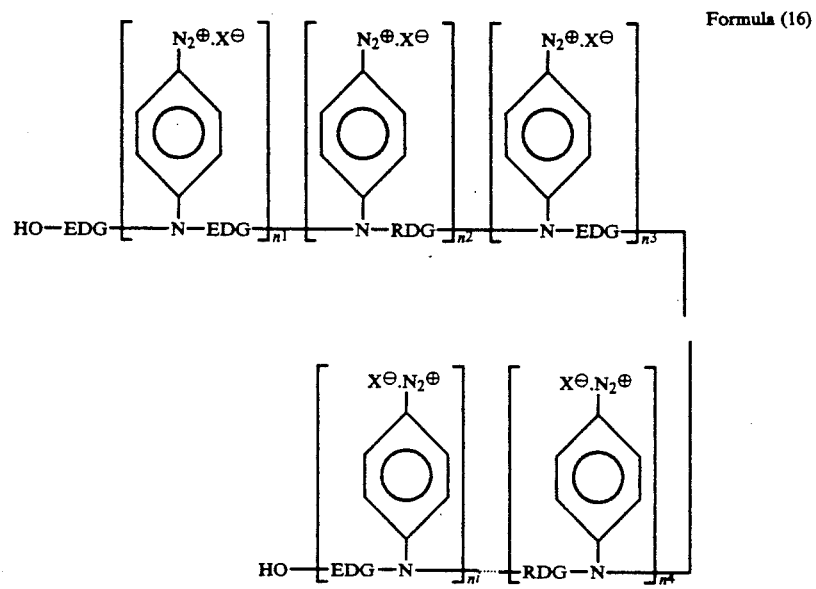

Formula (16)

wherein n and EDG are the same as those in Formula (13).

wherein n and EDG are the same as those in Formula (13); $n^1$ to $n^i$ denote an integer from 0 to 4; $n^1+n^2+\ldots n^i=2$ to 20; and RDG denotes an atomic group derived from resorcinol-diglycidylether.

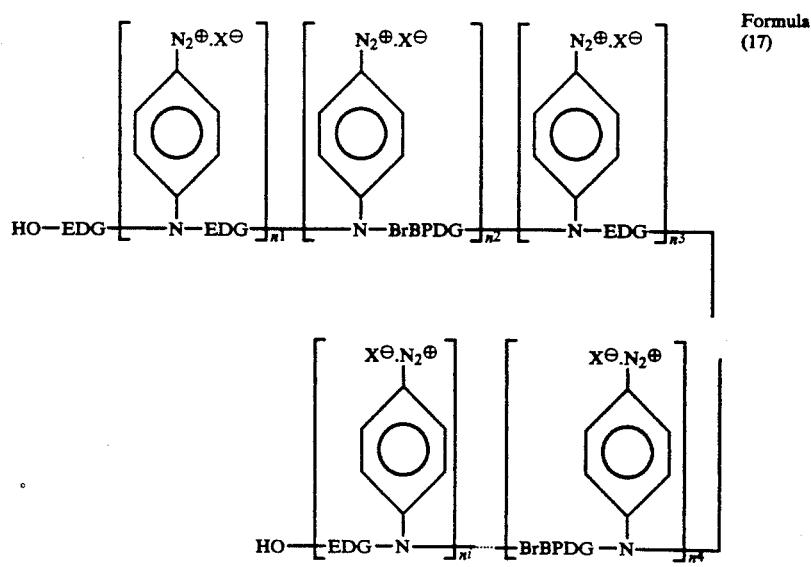

Formula (17)

wherein EDGE is the same as that in Formula (13); BrBPDG is the same as that in Formula (12); $n^1$ to $n^i$ denote an integer from 0 to 4; and $n^1+n^2+\ldots n^i=2$ to 20.

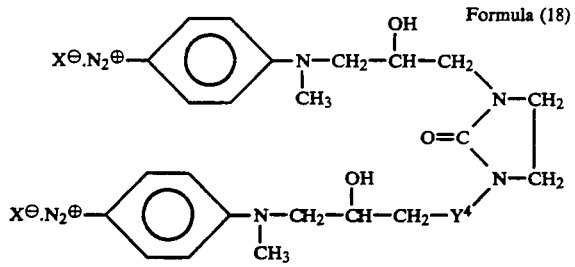

Formula (18)

wherein $Y^4$ does not exist or denotes a divalent group derived from a lower condensate of epichlorohydrin and ethyleneurea.

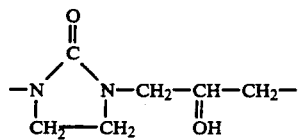

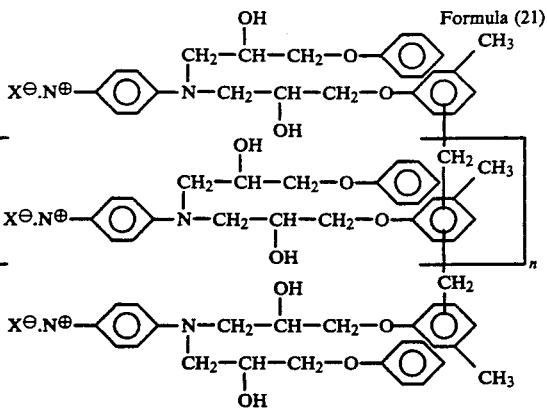

Formula (21)

wherein n is an integer from 1 to 8.

Formula (22)

Formula (19)

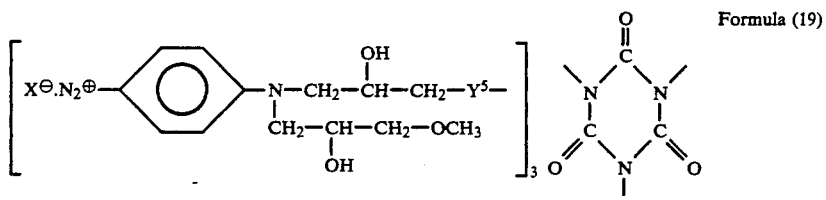

wherein $Y^5$ does not exist or denotes a divalent group derived from a lower condensate of epichlorohydrin and isocyanuric acid.

Formula (20)

-continued

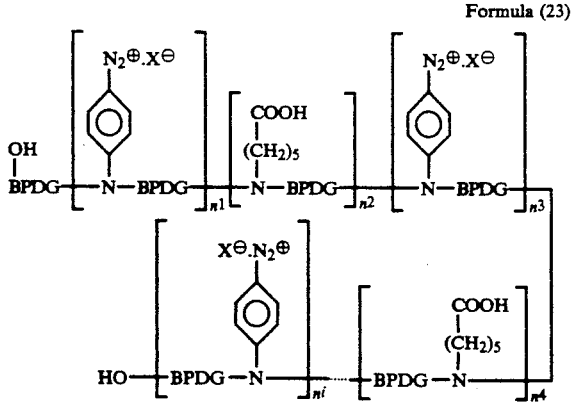

Formula (23)

wherein BPDG is the same as that in Formula (11); $n^1$ to $n^i$ denote an integer from 1 to 4; and $n^1+n^2+\ldots n^i=5$ to 20.

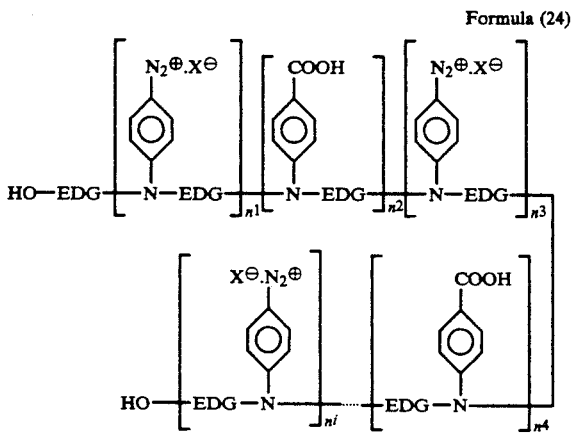

Formula (24)

wherein EDG is the same as that in Formula (13); and $n^1$ to $n^i$ denote the same as those in Formula (23).

Examples of compounds which are main ingredients of the novel aromatic diazo compound according to the present invention are shown in chemical formulas, however, it is difficult to industrially produce a single substance of the compound in a high-purity state. For example, it is difficult to industrially produce a diazo compound of Formula ($1_{m=0}$), in which m=0 in Formula (1), but the industrial production of a mixture mainly comprising the compound of Formula ($1_{m=0}$), with diazo compounds of larger molecular weights corresponding to m=1 to 8 in Formula (1).

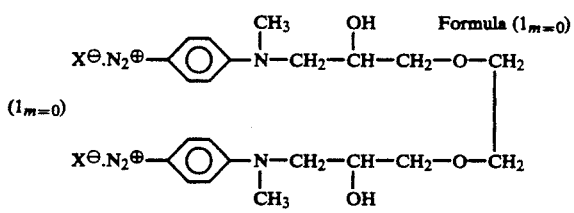

Formula ($1_{m=0}$)

This is because, as described in the production method (I) or (III) according to the present invention, ethyleneglycol-diglycidylether is an important raw material in the production of the compound of Formula (1), but it is difficult to industrially produce the diglycidylether in a high-purity state. As described above, the compound of Formula (1) is industrially obtained as a mixture. However, although being a mixture, these compounds are each a novel compound corresponding to the compound having two or more groups of Formula (I) in the molecule, and are thus suitable as photosensitive agents for the photosensitive composition.

The multifunctional diazo compound according to the present invention includes a variety of molecular structures as shown in Formulae (1) to (24), however, the ultraviolet spectral characteristics from the diazonium of these compounds are almost the same; aqueous solutions of these compounds have maximum absorption wavelengths λ max of the near-ultraviolet region in the range from 372 to 382 nm, but have no absorption in the visible region of 420 to 500 nm.

This is shown in FIG. 1 compared with a currently-used multifunctional diazonium compound having a basic structure of diphenylamine-4-diazonium salt.

Therefore, the diazo compound according to the present invention can be handled under a white light, which is an important advantage of the diazo compound in production and use as a photosensitive agent. Thus, the above-described object 1) has been achieved using the present invention.

As described above, the object 2) of the present invention is a matter of solubility of the diazo compound in organic solvents or water. As shown, the present invention enables various types of multifunctional diazo compounds of a variety of molecular structures. Since these various multifunctional diazo compounds of course have a variety of solubilities in organic solvents or water, the present invention can provide multifunctional diazo compounds having solubilities most suited for photosensitive lithographic printing plates or photosensitive screen printing plates.

Each of the diazo compounds according to the present invention is highly sensitive to light over conventional art "diazo resin." This is one of the most important advantageous characteristics of the diazo compounds according to the present invention, thereby solving the above-described fourth problem. FIG. 2 is a graph showing a photodegradation rate of the conventional "diazo resin" in an aqueous solution having a pH value of 3, compared with the multifunctional diazo compound according to the present invention.

A fifth advantage of the diazo compound of the present invention is that it is superior in storage stability to conventional "diazo resin." During storage, a diazo compound tends to react with contained moisture, resulting in decomposition. FIG. 3 shows the results of accelerated storage stability tests of Example 12, showing that the diazo compound according to the present invention is high in storage stability.

The novel aromatic diazo compounds according to the present invention can be easily produced using combinations of known synthesis reactions. As described in the production methods (I) to (VI) according to the present invention, a first-stage synthesis reaction of the process involves a reaction of an aniline homologue with glycidylether or glycidylamine compound. For example, the first-stage synthesis reaction of the production method (I) is shown below.

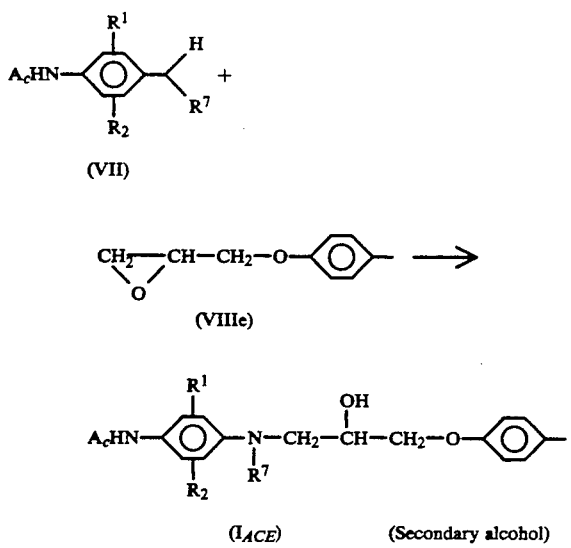

(VII)

(VIIIe)

($I_{ACE}$)  (Secondary alcohol)

It is known that a reaction of epoxy compound and amine generally forms two isomers: a secondary alcohol and a primary alcohol.

A typical example is the following reaction, in which, when the epoxy ring has a group having conjugated double bonds such as phenyl group or ethylene groups or an electron donative group, a primary alcohol tends to be formed (J. K. Addy, R. M. Laird, R. E. Parker; J. Chem. Soc., 1961, 1970).

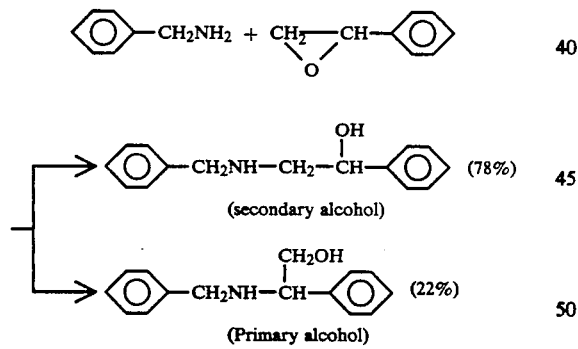

On the contrary, when there is an electron attractive group in the vicinity of the epoxy ring, a primary alcohol is hard to be formed. Since glycidylether has an electron attractive oxygen atom in the vicinity of the epoxy ring, the main product is a secondary alcohol, but a primary alcohol is hard to be produced (L. Shechter, J. Wymstra, R. P. Kurkiy; Ind.Eng.Chem.,48, 94(1956).

Therefore, the main product of the reaction between the compound of Formula (VII) and the compound of Formula (VIIIe) is a secondary alcohol of Formula ($I_{ACE}$), but a compound of Formula ($I_{ACEi}$), which is a primary alcohol, is hard to be formed.

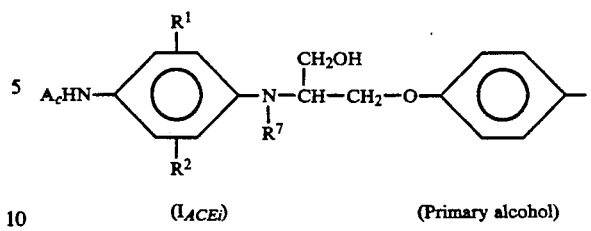

($I_{ACEi}$)  (Primary alcohol)

As a result, the novel aromatic diazo compound according to the present invention mainly comprises a compound having two or more groups (secondary alcohol) of Formula (I).

Chemical structure of Formula (I), which is the most important group of the novel aromatic diazo compound according to the present invention, is also identified experimentally as described in Example 18.

Examples of p-aminoacylanilide of Formula (VII) described in the production method (I) or (II) according to the present invention, but not limited to, are shown below:

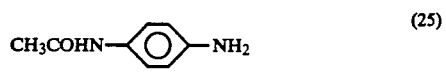
(25)

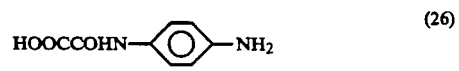
(26)

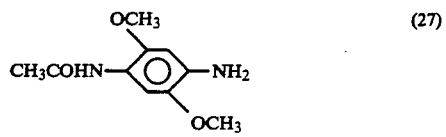
(27)

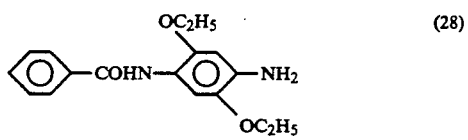
(28)

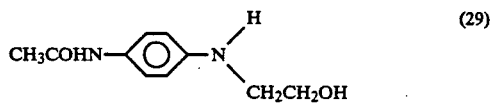
(29)

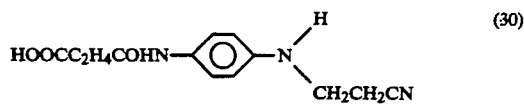
(30)

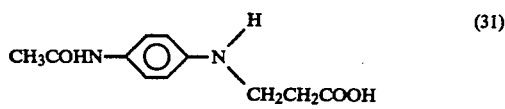
(31)

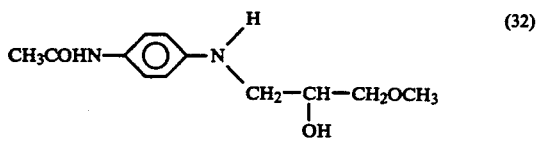
(32)

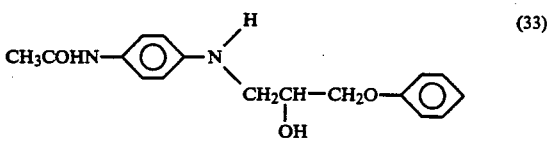
(33)

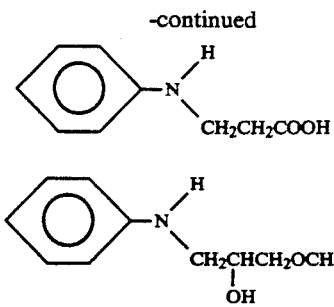 (34)

Examples of aniline or its homologue of Formula (X) described in the production method (III) or (IV) according to the present invention, but not limited to, are shown below:

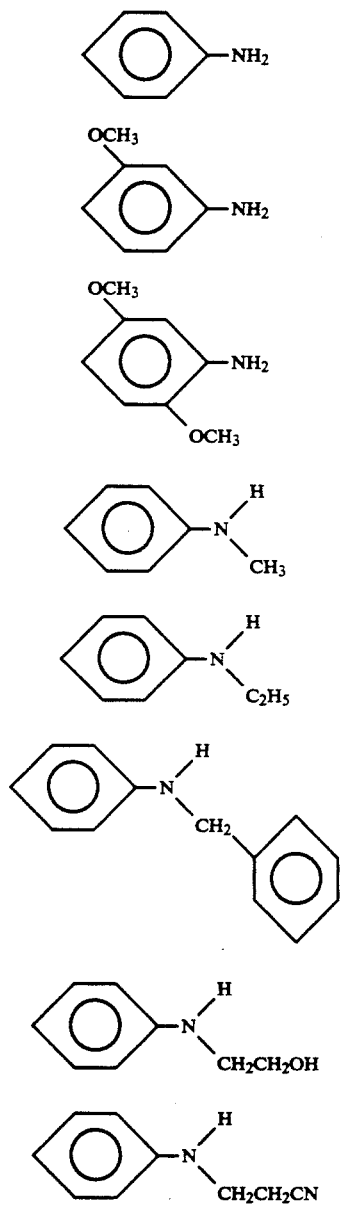

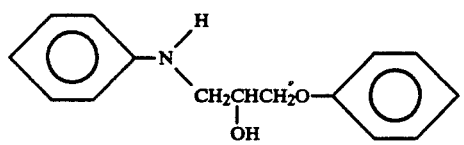 (43)

(44)

(45)

Examples of compounds having two or more glycidylether groups of Formula (VIII) or glycidylamino groups of Formula (IX) in the molecule, described in the production method (I) or (II) according to the present invention, but not limited to, are shown in the following Formula (46) to Formula (61):

In general, it is difficult to industrially produce a single compound of polyglycidylether or polyglycidylamine with a high purity. This is because the epoxy group in the glycidyl group is highly reactive, and sequential reactions of epoxy ring tend to take place during synthesis reactions of the compounds having glycidyl groups, producing polymeric side products. For example, a reaction of ethyleneglycol and epichlorohydrin to produce ethyleneglycol diglycidylether results in a mixture of Formula (46).

Formula (46)

wherein m is an integer from 0 to 20. The compound of Formula (46) in which m=0 is preferable for use in the synthesis of the novel diazo compound according to the present invention, but it is difficult to produce such a single compound industrially. However, a mixture mainly comprising the compound of m=0, with compounds of m=1 to 8, has no problem as a raw material of the compound according to the present invention. Such compounds are shown in Formula (47) to Formula (61).

Diglycidylether mainly comprising Formula (47) obtained by the condensation of 2,2-bis(4-hydroxyphenyl) propane (bisphenol A) and epichlorohydrin:

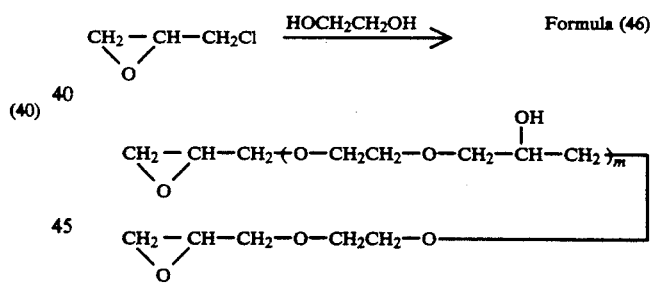

Formula (47)

Diglycidylether mainly comprising Formula (48) obtained by the condensation of 2,2-bis(4-hydroxy-3,5-dibromophenyl) propane (tetrabromo-bisphenol A) and epichlorohydrin:

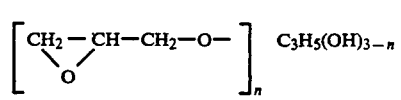

Formula (54)

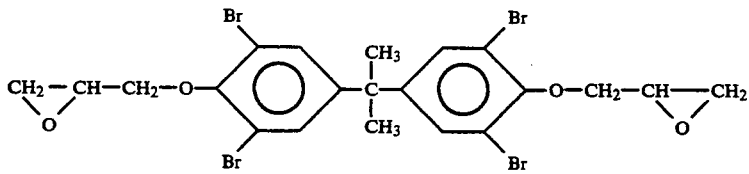

Formula (48)

Diglycidylether mainly comprising Formula (49) obtained by the condensation of bis(4-hydroxyphenyl) methane and epichlorohydrin:

Polyglycidylether mainly comprising Formula (55) obtained by the condensation of pentaerythritol and epichlorohydrin, wherein $C_5H_8(OH)_4$ denotes pentaerythritol, and n is 2 to 4:

Formula (49)

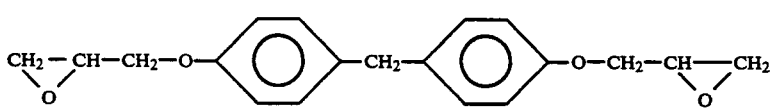

Diglycidylether mainly comprising Formula (50) obtained by the condensation of dihydroxybenzene and epichlorohydrin:

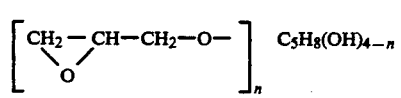

Formula (55)

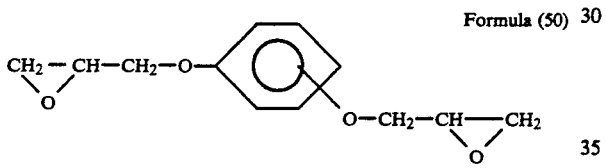

Formula (50)

Polyglycidylether mainly comprising Formula (56) obtained by the condensation of sorbitol and epichlorohydrin, wherein $C_6H_8(OH)_6$ denotes sorbitol, and n is an integer from 2 to 6:

Diglycidylether mainly comprising Formula (51) obtained by the condensation of bis(4-hydroxyphenyl) sulfone and epichlorohydrin:

Formula (51)

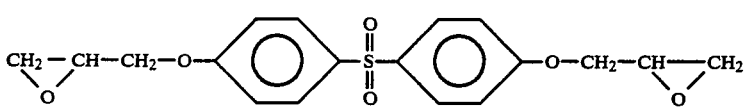

Diglycidylether mainly comprising Formula (52) obtained by the condensation of propyleneglycol and epichlorohydrin:

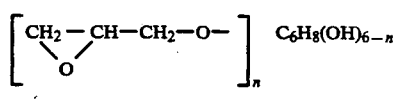

Formula (56)

Formula (52)

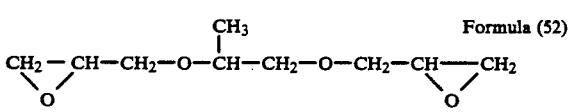

Polyglycidylether mainly comprising Formula (57) obtained by the condensation of phenol-formaldehyde condensate and epichlorohydrin, wherein PFR denotes a group of phenol-formaldehyde condensate molecule, with n units of phenolic OH removed, and n is an integer from 2 to 10:

Diglycidylether mainly comprising Formula (53) obtained by the condensation of 1,6-hexanediol and epichlorohydrin:

Formula (53)

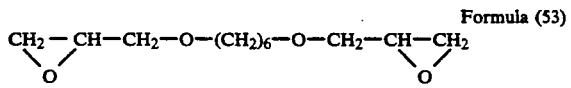

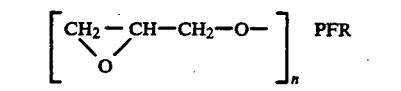

Formula (57)

Polyglycidylether mainly comprising Formula (54) obtained by the condensation of glycerin and epichlorohydrin, wherein $C_3H_5(OH)_3$ denotes glycerin, and n is 2 or 3:

A diglycidylamino compound mainly comprising Formula (58) obtained by the condensation of ethyleneurea and epichlorohydrin:

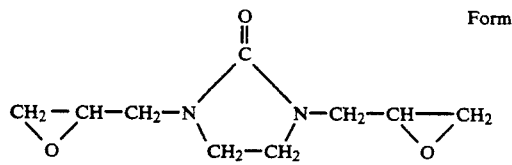

Formula (58)

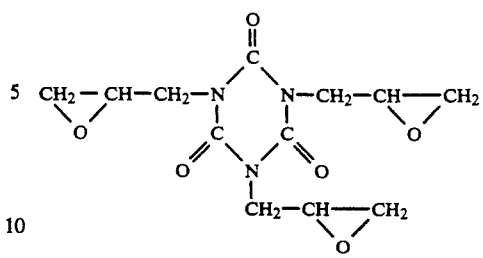

Formula (60)

A diglycidylamino compound mainly comprising Formula (59) obtained by the condensation of 4-chloroaniline and epichlorohydrin:

Formula (59)

Polyglycidylamino-diphenylmethane mainly comprising Formula (61) obtained by the condensation of 4,4'-diaminodiphenylmethane and epichlorohydrin:

Formula (61)

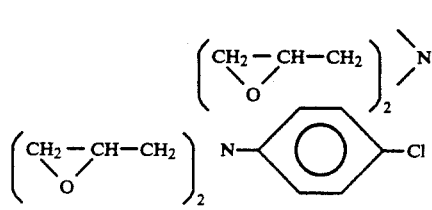

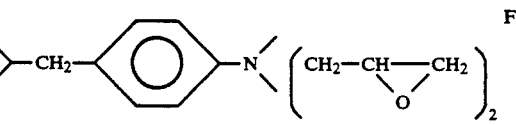

Polyglycidylisocyanate mainly comprising Formula (60) obtained by the condensation of isocyanuric acid and epichlorohydrin:

Examples of compounds having one or more groups of Formula (I) in the molecule, and reacting with a carbonyl reagent such as formaldehyde to form a condensation polymer, described in the production method (VII) according to the present invention, but not limited to, are shown in the following Formula (62) to Formula (65):

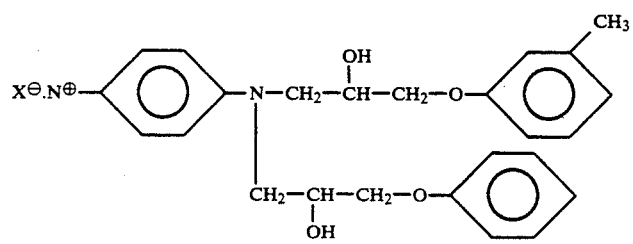

Formula (62)

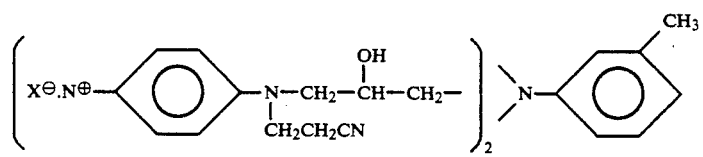

Formula (63)

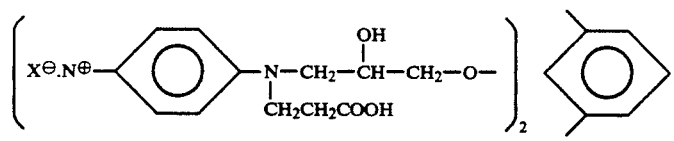

Formula (64)

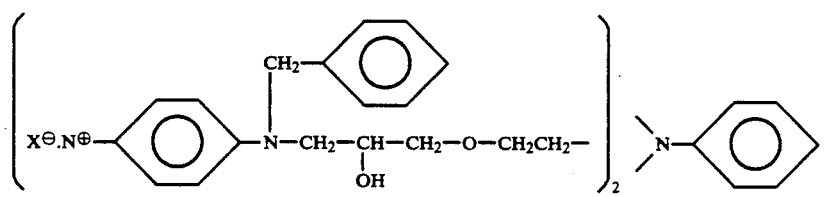

Formula (65)

Multifunctional diazo compounds obtained from compounds of Formulae (62) and (64) by condensation polymerization with formaldehyde are the compounds of Formula (21) and Formula (22), respectively.

Examples of compounds having one or more groups of Formula ($II_{AC}$) in the molecule, described in the production method (VIII) according to the present invention, but not limited to, are shown in the following Formula (66) to Formula (68):

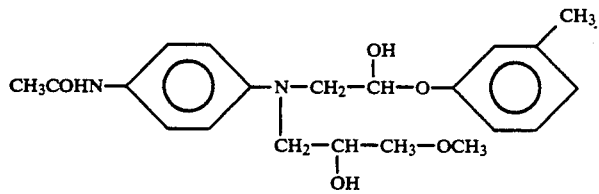

Formula (66)

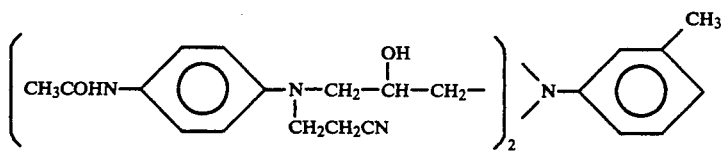

Formula (67)

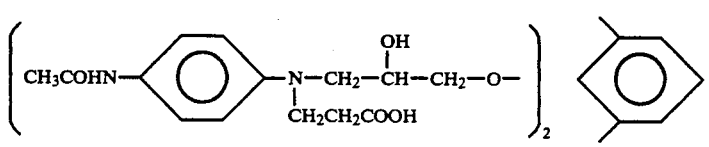

Formula (68)

Multifunctional diazo compounds obtained from compounds of Formulae (67) and (68) by condensation with formaldehyde, deacetylation, and diazotization are the compounds of Formula (20) and Formula (22), respectively.

As described above, the novel aromatic diazo compounds according to the present invention can be relatively easily produced by a combination of known synthesis reactions. Details of the synthesis method will be described in embodiments later, but briefly described below.

1) Since the reaction of an aniline homologue of Formula (VII) or (X) with a glycidyl compound having a group of Formula (VIII) or (IX) is an exothermic reaction, and tends to form side products at temperatures above 50° C., it is preferable to use external cooling to maintain the reaction temperature at 20° to 40° C.

Preferable reaction solvents include 2-methoxyethanol, 1-methoxy-2-propanol, 1,4-dioxane, dimethylacetamide, acetic acid, propionic acid, lactic acid, or mixtures thereof. Among these, the reaction proceeds smoothly in acetic acid or lactic acid.

In a reaction of an amine and epoxy compound, a carboxylic acid has a catalytic function to promote the reaction (Toshio Kakurai, Tatsuya Noguchi; Yuki Gosei Kagaku Zasshi 18, 485(1960), Kogyo Kagaku 63, 294(1960), 64, 398(1961)), and acetic acid is also preferable as a solvent for the aniline homologue of Formula (VII).

2) While either of alkaline hydrolysis or acid hydrolysis can be applied to the deacylation of a compound of Formula (II$_{AC}$) into a compound of Formula (II$_a$), the acid hydrolysis is advantageous in view of preceding and subsequent steps of this reaction. Sulfuric acid, hydrochloric acid, or phosphoric acid can be used for this reaction. There are many experimental examples of acid hydrolysis of acetanilide homologue (e.g. J. R. Johnson, T. Sandborn, Organic Synthesis Coll. Vol. I, 111), which can be applied to the present invention.

3) To convert a compound of Formula (II$_a$) by diazotization into a compound having a group of Formula (I), there is reported an industrial procedure of diazotization reaction of 4-amino-N,N-dimethylaniline (PB Report 74026 p.2963-5), which can be applied to the present invention.

4) Synthesis of a compound of Formula (II$_{NO}$) and its reduction into a compound of Formula (II$_a$) is also achieved according to an industrial synthesis method of 4-nitroso-N,N-dimethylaniline and its reduction.

The novel aromatic diazo compound obtained by the present invention mainly comprising a compound having two or more groups of Formula (I) has superior properties as a photosensitive agent, as described above. Therefore, by using the novel aromatic diazo compound according to the present invention as a photosensitive agent, various photosensitive compositions can be obtained which are novel and have superior properties. Among these various photosensitive compositions, but not limited to, photosensitive lithographic printing plate and photosensitive screen printing plate, and colored image formation photosensitive materials have advantageous properties, which will be described in detail.

The present invention, which uses the novel aromatic diazo compound, allows production of a photosensitive lithographic printing plate with improved properties. For example, in the production of a lithographic printing plate, the diazo compound according to the present invention can be used in combination with various natural or synthetic resins. These resins must be sufficiently ink-receptive, soluble in ordinary organic solvents, compatible with the aromatic diazo compounds according to the present invention, and have film-forming properties, as well as abrasion resistance and an adequate elasticity.

These resins include polymers of $\alpha,\beta$-unsaturated carboxylic acids such as cresol resin, polyester, polyamide, polyurethane, polyvinyl chloride, polymethacrylate, polystyrene, and polyvinyl acetate; and copolymers of polymerizable monomers selected from acrylates such as methyl acrylate, ethyl acrylate, and 2-hydroxyethyl acrylate, alkylmethacrylates, acrylamides such as acrylamide and N-ethylacrylamide, vinylethers, vinylesters, and styrenes.

Depending on the type of substrate and application purpose, the content of the inventive photosensitive diazo compound in the inventive photosensitive composition is preferably 1 to 50% by weight, more preferably 3 to 20% by weight.

In addition to the above-described ingredients, the photosensitive composition according to the present invention can be mixed with dyes, pigments, coating improvers, and plasticizers as necessary.

The dyes include, for example, triphenylmethane dyes, diphenylmethane dyes, oxazine dyes, xanthene dyes, iminonaphthoquinone dyes, azomethine dyes, and anthraquinone dyes, represented by Victoria Pure Blue BOH (Hodogaya Chemical), Oil Blue #603 (Orient Chemical), Patent Pure Blue (Sumitomo Mikuni Kagaku), Crystal violet, Brilliant green, Ethyl violet, Methyl green, Erythrosin B, Basic flosin, Malachite green, Oil red, m-Cresol purple, Rhodamine B, Auramine, 4-p-diethylaminophenylimino-naphthoquinone, and cyano-p-diethylaminophenyl-acetanilide.

The dye is contained normally in an amount of approximately 0.5 to 10% by weight, preferably in an amount of approximately 1 to 5% by weight, in the photosensitive composition.

The coating improvers include alkylethers (e.g. ethylcellulose, methylcellulose), fluorine-containing surfactants (e.g. Florad FC-430 (Sumitomo 3M)), and nonionic surfactants (e.g. Pluronic L-64 (Asahi Denka)); the plasticizers, which give the coating film flexibility and abrasion resistance, include, for example, butylphthalyl, polyethylene glycol, tributyl citrate, diethyl phthalate, dibutyl phthalate, dihexyl phthalate, dioctyl phthalate, tributyl phosphate, trioctyl phthalate, tetrahydrofurfuryl oleate, and oligomers of acrylic acid or methacrylic acid; oil sensitizing agents, which improve the oil sensitivity of the image portion, include, for example, a half-ester of a styrene-maleic anhydride copolymer with alcohol described in Japanese Patent Publication 55-527/1980; stabilizers include, for example, polyacrylic acid. tartaric acid, phosphoric acid, phosphorous acid, and organic acids (acrylic acid, methacrylic acid, citric acid, oxalic acid, benzenesulfonic acid, naphthalenesulfonic acid, 4-methoxy-2-hydroxybenzophenone-5-sulfonic acid). Depending on the purpose, these additives are generally added in amounts of 0.01 to 30% by weight based on the solid ingredients.

The above-described photosensitive composition can be coated over the entire surface of the substrate to obtain a photosensitive lithographic printing plate.

As the substrate is used a sheet of paper, plastic, or aluminum, which is suitable for use in the lithographic printing plate.

The coating solvents include cellosolves such as methylcellosolve, 1-methoxy-2-propanol, methylcellosolve acetate, ethylcellosolve, and ethylcellosolve acetate, dimethylformamide, dimethylsulfoxide, dioxane, acetone, cyclohexanone, trichloroethylene, and methylethyl ketone. These solvents can be used alone or as mixture.

The composition can be coated, for example, by rotary coating, wire bar coating, dip coating, air knife coating, roll coating, blade coating, or curtain coating. The composition is preferably coated in an amount of 0.2 to 10 $g/m^2$ as solid.

An aluminum plate is particularly preferable as the substrate to form a photosensitive composition layer on top. However, when an untreated aluminum plate is used, adhesion of the photosensitive composition is poor, or the photosensitive composition tends to decompose. Various methods have been proposed to eliminate these problems, for example, the surface of aluminum plate is grained, and then treated with a silicate salt (U.S. Pat. No. 2,714,066), treated with sulfonic acids and their derivatives (U.S. Pat. No. 3,220,832), treated with potassium hexafluorozirconate (U.S. Pat. No. 2,946,683), or subjected to anodic oxidation, or, after anodic oxidation, treated with an aqueous solution of alkali metal silicate (U.S. Pat. No. 3,181,461).

In the present invention, it is preferable that the aluminum plate to form the photosensitive composition layer on top is grained, anodized, and pores formed by anodized oxidation are sealed. Graining is achieved, after degreasing the aluminum plate surface, by brushing, chemical treatment, or electrolytic etching.

Anodic oxidation uses a solution containing one or more selected from sulfuric acid, chromic acid, oxalic acid, and malonic acid, and electrolyzes the aluminum plate as the anode. The amount of the thus formed anodic oxidation film is adequately 1 to 50 $mg/dm^2$, preferably 10 to 40 $mg/dm^2$. The amount of the anodic oxidation film can be determined, for example, by dipping the plate in a phosphoric and chromic acid solution (35 ml of 85% phosphoric acid aqueous solution and 20 g of chromium (VI) oxide dissolved in 1 liter of water) to dissolve the oxide film, and measuring a change in weight between before and after the film removal.

Sealing is achieved by treating with boiling water, steam, sodium silicate, or a bichromate aqueous solution. In addition, the aluminum substrate can be primer treated with aqueous solution of a water soluble polymer compound or a metal salt such as of fluorozirconate.

The thus treated aluminum substrate can be coated with the photosensitive composition to obtain a photosensitive printing plate. In particular, the use of the substrate results in improved storage stability and adhesion of the photosensitive composition layer, and gives sharp images after exposure and development to obtain a printed matter having a sharp image during an extremely long printing process.

The thus obtained photosensitive lithographic printing plate can be used by a conventional method known in the art. Typically, the photosensitive printing plate is closely contacted with a negative film and exposed, and developed with a weak alkaline aqueous solution containing a small quantity (10 wt. % or less) of organic solvent to obtain a printing plate. The lithographic printing plate can be used on a sheet-fed or web offset printing press.

Thus, the photosensitive printing plate is exposed through a transparent original picture having line images or dot images, and developed with an aqueous developing solution to obtain a negative image to the original picture. Light sources suitable for the exposure include an ultrahigh pressure mercury lamp, a carbon arc lamp, a xenon lamp, and a metal halide lamp.

The developing solution used for developing the photosensitive lithographic printing plate obtained using the photosensitive composition according to the present invention can be any of known developing solutions, preferably containing a specific organic solvent, an alkaline agent, and water as essential ingredients. The specific organic solvent is one which, when contained in the developing solution, can dissolve or decompose unexposed (non-image) portions of the photosensitive composition, and has a solubility of no more than 10% by weight in water at room temperature (20° C.). Any organic solvent having the above properties may be used. Such organic solvents include, but are not limited to, carboxylic acid esters such as ethyl acetate, propyl acetate, butyl acetate, amyl acetate, benzyl acetate, ethyleneglycol-monobutylacetate, butyl lactate, and butyl levulinate; ketones such as ethylbutylketone, methylisobutylketone, and cyclohexanone; alcohols such as ethyleneglycol-monobutylether, ethyleneglycol-benzylether, ethyleneglycol-monophenylether, benzyl alcohol, methylphenyl carbinol, n-amyl alcohol, and methylamino alcohol; alkyl-substituted aromatic hydrocarbons such as xylene; and halogenated hydrocarbons such as methylene-dichloride, ethylene-dichloride, and monochlorobenzene. Among these organic solvents, ethyleneglycol-monophenylether and benzyl alcohol are particularly effective. These organic solvents are contained in the developing solution normally in an amount of 1 to 20% by weight, preferably 2 to 10% by weight.

The alkaline agent used in the developing solution includes:

(A) inorganic alkaline agents such as sodium silicate, potassium silicate, potassium hydroxide, sodium hydroxide, lithium hydroxide, sodium or ammonium phosphate or hydrogen phosphate, sodium metasilicate, sodium carbonate, and ammonia;

(B) organic compounds such as mono-, di-, or trimethylamine, mono-, di, or triethylamine, mono- or diisopropylamine, n-butylamine, mono-, di-, or triethanolamine, mono-, di-, or triisopropanolamine, ethyleneimine, and ethylenediamine.

Among these alkaline agents, (A) potassium silicate and sodium silicate, and (B) organic amines are preferable, and (A) sodium silicate and (B) di- or tri-ethanolamine are particularly preferable.

These alkaline agents are contained in the developing solution in an amount of 0.05 to 8% by weight.

Furthermore, in order to improve the storage stability and printing resistance, it is preferable to add a water-soluble sulfite salt to the developing solution as necessary. Such a water-soluble sulfite salt is preferably selected from alkali or alkaline earth metal salts of sulfurous acid such as sodium sulfite, potassium sulfite, lithium sulfite, and magnesium sulfite. These sulfite salts are added to the developing solution composition normally in an amount of 0.05 to 4% by weight, preferably 0.1 to 1% by weight.

To facilitate dissolution of the organic solvent in water, a solubilizing agent can be added. As such a solubilizing agent, low molecular weight alcohols or ketones can be used, which are more water-soluble than the organic solvent used. An anionic surfactant or an amphoteric surfactant can also be used. Such alcohols and ketones include methanol, ethanol, propanol, butanol, acetone, methylethylketone, ethyleneglycol-monomethylether, ethyleneglycol-ethylether, methoxyethanol, methoxypropanol, 4-methoxymethylbutanol, and N-methylpyrrolidone, which are preferably used. As a surfactant, it is preferable to use, for example, sodium isopropylnaphthalene-sulfonate, sodium n-butylnaphthalene-sulfonate, sodium N-methyl-N-pentadecylaminoacetate, or sodium laurylsulfate. The content of these alcohols or ketones is not specifically limited, but preferably no more than 30% by weight of the developing solution.

The photosensitive composition according to the present invention is highly photosensitive and highly wear resistant to printing, and can be rapidly developed with a weak alkaline aqueous solution. Furthermore, it can be easily developed since it has a wide range of optimum developing conditions (so-called developing latitude).

Another embodiment of the photosensitive composition according to the present invention is a photosensitive material for screen printing plates.

The inventive diazo compound is mixed with a water-soluble resin (e.g. polyvinyl alcohol, polyvinyl alcohol with pendant styrylpyridinium groups, or the like) to obtain a screen printing photosensitive solution. In addition, a polyvinyl acetate emulsion or a vinyl monomer such as acrylate, diacrylate, or triacrylate of alcohols can be added.

The photosensitive composition is coated on a screen mesh comprising a synthetic resin such as polystyrene, a synthetic resin deposited with a metal such as nickel, or stainless steel, and then dried. This procedure can be repeated to obtain a screen printing plate with a thickness of 10 to 400 $\mu$m.

With the photosensitive composition according to the present invention, a screen printing plate having a high photosensitivity and high ink resistance can be obtained.

Another embodiment of the photosensitive composition according to the present invention is a colored image formation material.

The transparent substrate used in the present invention includes those films of polyethylene terephthalate, polypropylene, polyethylene, polyvinyl chloride, polystyrene, polycarbonate, and cellulose triacetate.

Film-forming water-soluble polymeric substances, which become insoluble when irradiated with light, and can be dissolved with water alone, include a variety of substances such as polyvinyl alcohol, gelatin, casein, glue, alginic acids, gums, cellulose derivatives such as carboxymethyl cellulose and hydroxyethyl cellulose, polyacrylic acid and its salts, polymethacrylic acid and its salts, polyacrylamide, polyethyleneoxide, polyvinylpyrrolidone, and the like.

The coloring agent can be selected from a variety of water-dispersible pigments. Furthermore, water-soluble or alcohol-soluble dyes can also be used.

In addition to the above ingredients, the colored layer, which becomes insoluble when irradiated, can contain a stabilizer to prevent a dark reaction, and a leveling agent, an antifoamer, and a surfactant to improve applicability to provide the colored layer on the transparent substrate as necessary.

When the colored layer is formed, the above ingredients are normally dissolved or dispersed in water, but a water-soluble organic solvent such as alcohol can be used in part as a diluent to improve the coating quality as necessary.

The colored layer is preferably to be as thin as possible in view of resolution such as the tone reproduction, but preferably to be as thick as possible in view of dyeability. Thus, the optimum thickness is 2 to 5 $\mu$m to balance both. The colored layer can be provided directly on the transparent substrate, but it is effective to provide an intermediate layer between the colored layer and the substrate to improve adhesion as necessary. It is particularly preferable to provide an intermediate layer mainly comprising a synthetic resin such as polyester, polyvinylidene chloride, or polyurethane when polyethylene terephthalate film is used as a substrate, because the colored layer tends to have insufficient adhesion to this kind of film.

The colored layer and the intermediate layer may be formed on the substrate by a conventional method known in the art, not limited as far as a uniform coating film with no pinholes can be obtained.

Any type of light source can be used to insolubilize the photosensitive material according to the present invention, and usable light sources include various types of mercury lamps, a carbon arc lamp, a xenon lamp, a metal halide lamp, a chemical fluorescent lamp, and the like.

Furthermore, the diazo compound according to the present invention can be mixed with a hydrophilic or hydrophobic binder resin to obtain photosensitive compositions, which can be widely used for applications to form developable patterns. These photosensitive compositions can further contain coloring materials such as dyes or pigments. Potential applications include photoresist materials, photomasks, correction materials, second master materials, and the like.

DESCRIPTION OF THE PREFERRED EMBODIMENTS

Figure 1:
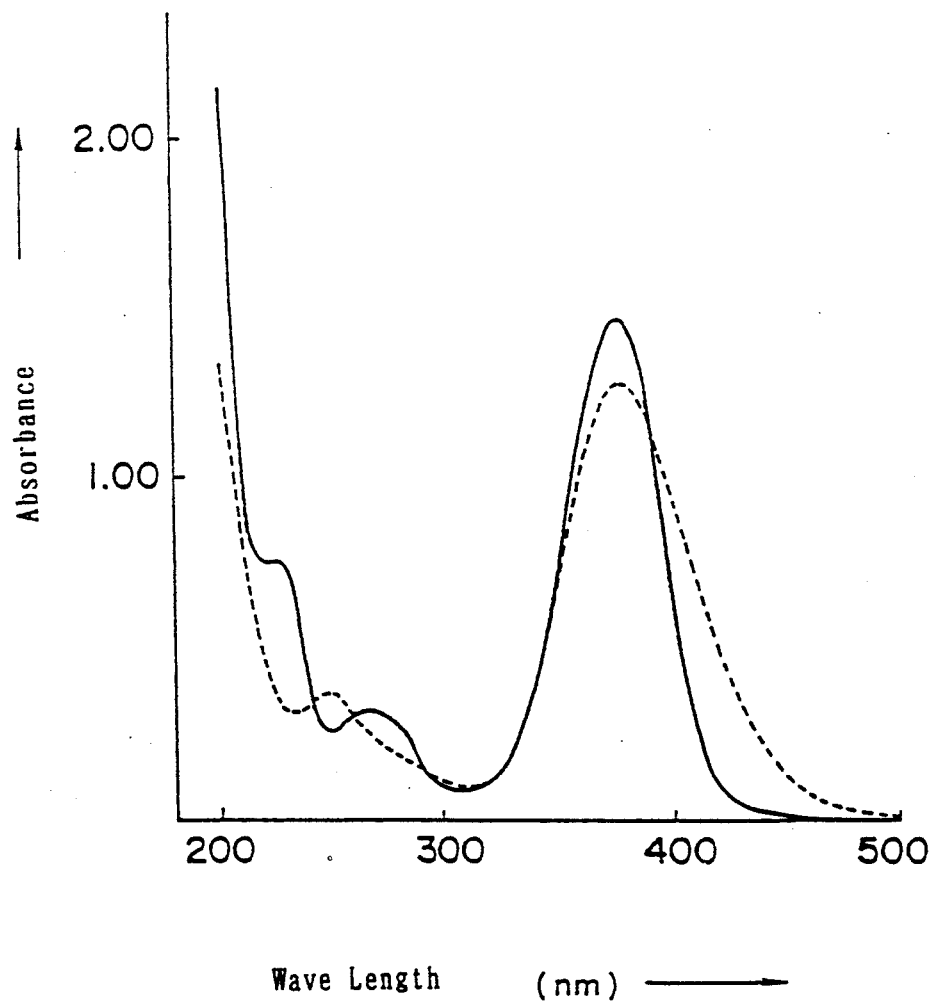
FIG. 1 is a UV absorption spectrum of the diazo compound synthesized in Example 4 and diphenylamine-4-diazonium salt/formaldehyde condensate synthesized in Comparative Example 1.

The present invention will now be described with reference to the preferred embodiments, but the present invention is not limited to the embodiments.

Examples 1 to 9 are synthesis examples of the aromatic diazo compounds according to the present invention.

Examples 10 to 12 are measurements of important properties of the aromatic diazo compounds according to the present invention.

Examples 13 to 17 show photosensitive compositions using the aromatic diazo compounds according to the present invention.

Example 18 is a basic experiment to confirm the chemical structure of the aromatic diazo compound according to the present invention. As previously described, the polyglycidyl compound, which is one of the main raw materials of the inventive compounds, is a mixture, and it is difficult to obtain a single pure compound. Therefore, the aromatic diazo compound according to the present invention is also obtained as a mixture, and it is difficult to confirm its chemical structure as a single compound. Then, in Example 18, a special glycidyl compound, which can be easily obtained as a single compound, was used to conduct a basic experiment of the present invention, and the resulting compound was determined for chemical structure. Through this experiment, the chemical structure of the main ingredient of the aromatic diazo compound according to the present invention could be confirmed.

EXAMPLE 1

Synthesis of aromatic diazo compound (11)

p-Aminoacetanilide, 15.0 g (0.1 mole), was dissolved in 90 g of acetic acid, 40.5 g of bisphenol A diglycidylether with an epoxy equivalent of 184 was dropped at 25° to 30° C. under agitation, and agitation was continued for 3 hours at approximately 30° C. and then for 6 hours at approximately 40° C. Hydrochloric acid, 50 g (35%), was added and agitated at 75° C. for 8 hours to achieve deacetylation.

After cooling to approximately 50° C., 350 g of methylcellosolve were added, cooled to 5° C. under efficient agitation, and 7.3 g of sodium nitrite (0.105 mole) was dissolved in 15 g of water and slowly dropped at a reaction temperature of 5° C. Agitation was continued for 1 hour at the same temperature to complete diazotization and then the diazotized solution was poured into 2 kg of 10% salt water cooled to 5° C., and the precipitated granular object material was filtered. The precipitate was dissolved in 250 g of methylcellosolve, and insolubles filtered out. The solution was poured into 1.5 kg of 10% salt water cooled to 5° C., the precipitated object substance filtered, washed with a small amount of isopropyl alcohol, and dried under vacuum. The yield was 40 g.

Aqueous solution of the diazo compound had a $\lambda_{max}$ of near-ultraviolet spectrum of 378 nm, and an absorption coefficient of 54.7 where concentration is in g/liter and optical path length in cm.

EXAMPLE 2

Synthesis of aromatic diazo compound (12)

p-Aminoacetanilide, 15.0 g (0.1 mole), was dissolved in 180 g of acetic acid and 78.3 g of tetrabromobisphenol A diglycidylether powder with an epoxy equivalent of 356 were added little by little at 25° to 30° C. under agitation, and agitation was continued for 8 hours at approximately 25° C. and then for 8 hours at approximately 45° C. Methylcellosolve, 250 g, was added, then 40 g of 95% sulfuric acid added little by little and agitated at 75° C. for 8 hours to achieve deacetylation.

The reaction mixture was diluted with 450 g of methylcellosolve, cooled to 3° to 5° C., and nitroslylsulfuric acid, produced by dissolving 7.7 g of sodium nitrite (0.11 mole) in 160 g of 95% sulfuric acid, was added at 3° to 5° C., and agitation continued for 1 hour. The result was poured into 5 kg of ice water, and the precipitated material was filtered. The precipitate was washed twice with cold water, and then with a small amount of isopropyl alcohol, and dried under vacuum. The yield was 84 g.

Methylcellosolve solution of the diazo compound had a $\lambda_{max}$ of near-ultraviolet spectrum of 382 nm, and an absorption coefficient of 31.5 where concentration is in g/liter and optical path length in cm.

EXAMPLE 3

Synthesis of aromatic diazo compound (17)

p-Aminoacetanilide, 15.0 g (0.1 mole), was dissolved in 80 g of acetic acid and 23.5 g of tetrabromobisphenol A diglycidylether powder with an epoxy equivalent of 356 were added little by little at 25° to 30° C. under agitation, and agitation was continued for 3 hours at approximately 30° C. Ethyleneglycol-diglycidylether, 17.7 g (an epoxy equivalent of 115), was added dropwise at the same temperature, agitation was continued for 6 hours at 40° to 45° C., 50 g of 35% hydrochloric acid were added, and the mixture was agitated at 75° C. for 8 hours to achieve deacetylation.

After cooling to approximately 50° C., 40 g of water were added, cooled to 3° to 5° C., 7.6 g (0.11 mole) of sodium nitrite (0.11 mole) dissolved in 20 g of water were slowly dropped at 3° to 5° C. After the completion of addition, agitation was continued for 1 hour to achieve diazotization.

Ammonium hexafluorophosphate, 18.0 g (0.11 mole), was dissolved in 150 g of water and dropped with the diazotized solution at 5° to 10° C. under agitation. After 30 minutes, 150 g of water were dropped, agitated for 1 hour, and the precipitated object material was filtered. The precipitate was washed twice with isopropylether, and dried under vacuum. The yield was 55 g.

2-Methoxyethanol solution of the diazo compound had a $\lambda_{max}$ of UV spectrum of 382 nm, and an absorption coefficient of 44.9 where concentration is in g/liter and optical path length in cm. This diazo compound is a multifunctional aromatic diazo compound of Formula (17) wherein $X^-$ is $PF_6^-$.

EXAMPLE 4

Synthesis of aromatic diazo compound (10)

p-Cyanoethylaminoacetanilide, 20.3 g (0.1 mole), was dissolved in 60 g of acetic acid and 18.5 g of polyglycidylether of phenol-formaldehyde resin with an epoxy equivalent of 175 were added, and reacted at 30° to 35° C. for 4 hours, and then at 40° to 45° C. Sulfuric acid, 70 g (40%), was added, and the mixture was agitated at 75° to 80° C. for 12 hours for deacetylation of acetylamino group and hydrolysis of cyanoethyl group into carboxyethyl group. Water, 100 g, was added, cooled to 3° to 5° C. and a solution of 7.3 g (0.105 mole) of sodium sulfite and 15 g of water was dropped in about 1 hour at the same temperature, and agitated for 30 minutes to complete diazotization.

The diazotized solution was poured into 400 g of 15% salt solution at 5° C. under agitation to liberate a paste-like diazo compound. This paste-like substance was removed, and kneaded with isopropyl alcohol to convert it into a powder.

The diazo compound powder was filtered, washed twice with isopropyl alcohol, and dried under vacuum. The yield was 32 g. Aqueous solution of the diazo compound had a λmax of near-ultraviolet spectrum of 374 nm, and an absorption coefficient of 64.1 where concentration is in g/liter and optical path length in cm.

This diazo compound has remarkably better storage stability in the presence of water, compared to conventional diphenylamine-based diazo compounds.

Figure 4:
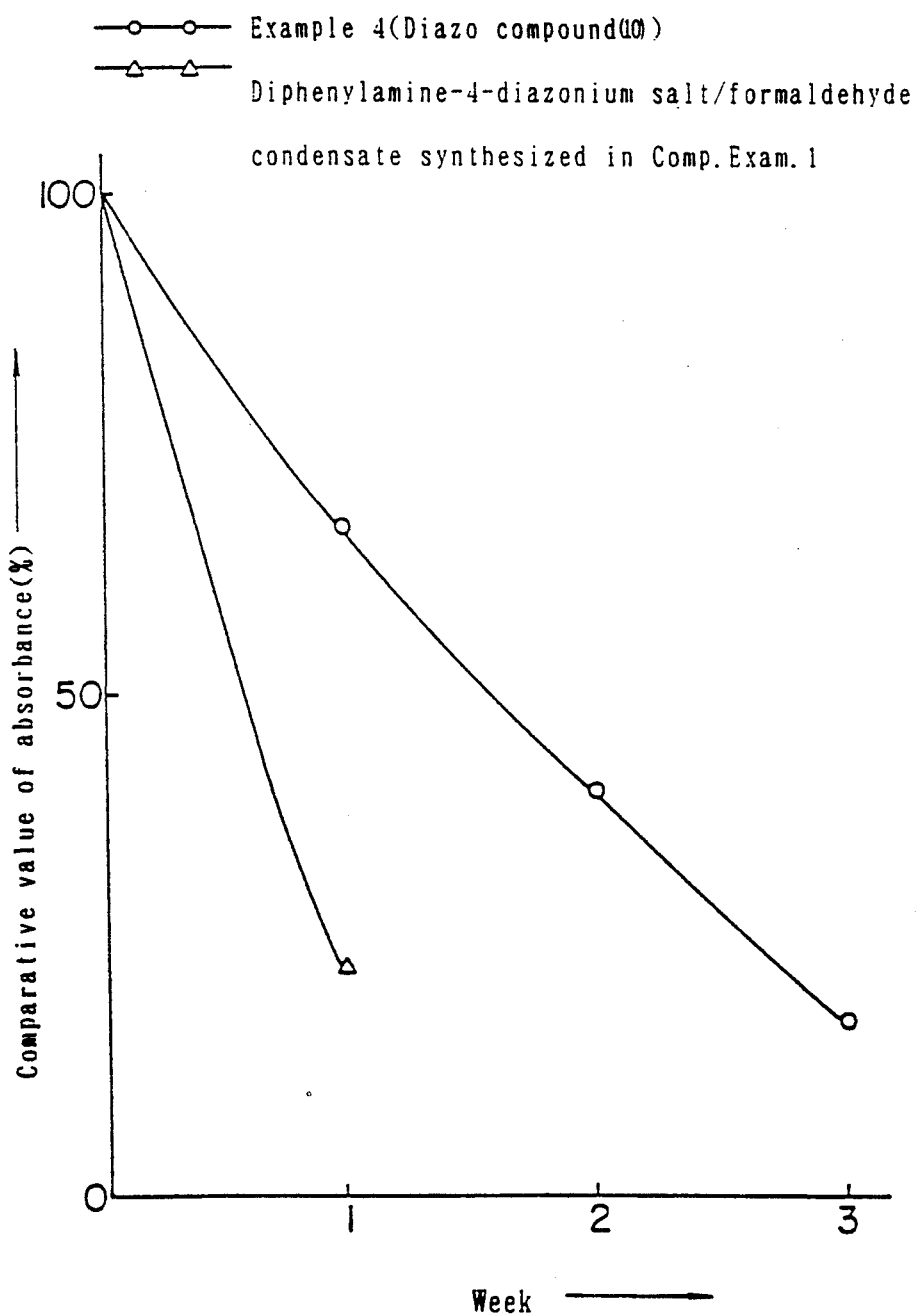
FIG. 4 is a graph showing storage stability of the diazo compound synthesized in Example 4 in aqueous solution of pH=3.

Experimental results of storage stability in aqueous solution with a pH value of 3, using the same procedure as in Example 12, are shown in FIG. 4.

EXAMPLE 5

Synthesis of aromatic diazo compound (19)

p-Aminoacetanilide, 15.0 g (0.1 mole), was dissolved in 70 g of acetic acid and 10.5 g of triglycidyl-isocyanurate with an epoxy equivalent of 100 were added little by little at 25° to 30° C. under agitation, 9.6 g of glycidylmethylether with an epoxy equivalent of 91 were dropped at 25° C., and the mixture was agitated at 30° C. for 12 hours. Hydrochloric acid, 50 g (35%), was added and agitated at 75° C. for 8 hours to complete deacetylation, 100 g of water were added, cooled to 3° to 5° C. under efficient agitation and 7.6 g (0.11 mole) of sodium nitrite dissolved in 20 g of water were slowly dropped at 3° to 5° C., and, after the completion of dropping, agitation was continued for 1 hour at the same temperature to complete diazotization.

The diazotized solution was poured into about 2 liters of isopropyl alcohol cooled to approximately 10° C. under agitation, and the precipitated solid substance was filtered, washed twice with isopropyl alcohol, and dried under vacuum. The yield was 26 g.

Aqueous solution of the diazo compound had a $\lambda_{max}$ of near-ultraviolet spectrum of 376 nm, and an absorption coefficient of 78.9 where concentration is in g/liter and optical path length in cm.

EXAMPLE 6

Synthesis of aromatic diazo compound (1)

N-Methylaniline, 21.4 g (0.2 mole), was dissolved in 80 g of acetic acid and 25.3 g of ethyleneglycoldiglycidylether with an epoxy equivalent of 115 were dropped at 25° to 30° C. The mixture was agitated at 25° C. for 4 hours and then at 40° C. for 6 hours, 130 g of 20% hydrochloric acid were added, cooled to 5° C. and 14.5 g (0.21 mole) of sodium nitrite dissolved in 40 g of water were slowly dropped in 30 minutes for nitrosation. Hydrochloric acid, 250 g (20%), and 150 g of water were added, while externally cooling to maintain the temperature at 35° to 40° C., and 33 g of zinc powder were slowly added to reduce the nitroso compound, obtaining a colorless, transparent solution. Activated charcoal, 50 g, was added and efficiently agitated and filtered. The filtrate was cooled to 5° C. and 14.5 g (0.21 mole) of sodium nitrite dissolved in 40 g of water were slowly dropped at the same temperature, and, after the completion of dropping, agitated for 1 hour to complete diazotization, 80 g of salt were slowly added under efficient agitation to achieve salting out. The salted-out diazonium-zinc chloride double salt was filtered, washed once with 15% salt solution and once with isopropyl alcohol, and dried under vacuum. The yield was 36 g.

Aqueous solution of the diazo compound had a $\lambda_{max}$ of near-ultraviolet spectrum of 376 nm, and an absorption coefficient of 84.1 where concentration is in g/liter and optical path length in cm. (This is an example of the production method (III) of aromatic diazo compound according to the present invention.)

EXAMPLE 7

Synthesis of aromatic diazo compound (21)

Diazo compound of Formula (62), 26.6 g (0.05 mole), wherein $X^-$ is $HSO_4^-$, was dissolved in 40 g of ice-cooled concentrated sulfuric acid, and 1.2 g (0.04 mole) of paraformaldehyde were slowly added so as the reaction temperature not to exceed 10° C., followed by agitation at 5° to 8° C. for 2 hours. The reaction solution was dropped into 300 g of isopropyl alcohol cooled to 3° C. The resulting precipitate was filtered, washed with isopropyl alcohol at 3° to 5° C., and dried under vacuum. The yield was 18.1 g.

Aqueous solution of the diazo compound had a $\lambda_{max}$ of near-ultraviolet spectrum of 377 nm, and an absorption coefficient of 63.4 where concentration is in g/liter and optical path length is in cm. (This is an example of the production method (VII) of aromatic diazo compound according to the present invention.)

EXAMPLE 8

Synthesis of aromatic diazo compound (22)

The compound of Formula (68), 33.4 g (0.05 mole), was dissolved in 150 g of 85% phosphoric acid and 0.8 g (0.027 mole) of paraformaldehyde were dissolved at 30° to 35° C. The mixture was agitated at the same temperature for 18 hours to complete condensation reaction with formaldehyde, and the temperature was increased to 80° C. and agitated for 8 hours for deacetylation, 200 g of water were added, cooled to 3° to 5° C., and 7.6 g (0.011 mole) of sodium nitrite dissolved in 20 g of water were slowly dropped at 3° to 5° C. under agitation, followed by agitation for 1 hour for diazotization, 5 g of activated charcoal were added and agitated, and 5 g of diatomaceous earth were added and filtered. The filtrate was poured into 150 g of 20% sodium tetrafluoroborate aqueous solution, precipitated diazo compound was washed three times with isopropyl alcohol, and vacuum dried. The yield was 26.2 g.

This crystal is the compound of Formula (22) wherein $X^-$ is $BF_4^-$. (This is an example of the production method (VIII) of aromatic diazo compound according to the present invention.)

EXAMPLE 9

Synthesis of aromatic diazo compound (24)

p-Aminoacetanilide, 9.0 g (0.06 mole), and 6.6 g (0.04 mole) of ethyl-p-aminobenzoate were dissolved in 60 g of acetic acid and 25.3 g of ethyleneglycol-diglycidylether with an epoxy equivalent of 115 were added at 25° to 30° C. The mixture was agitated at about 30° C. for 3 hours and then at 40° to 45° C. for 6 hours. Hydrochloric acid, 35 g (35%), was added, and agitated at 75° to 78° C. for 10 hours for deacetylation of the acetylamino group and hydrolysis of the ethylbenzoate. The result was diluted with 70 g of water, cooled to 3° to 5° C. and 4.5 g (0.065 mole) of sodium nitrite dissolved in 10 g of water were dropped under agitation for diazotization.

When the diazotized solution was poured into 400 g of 15% salt water at 5° C. under agitation, a paste-like diazo compound was liberated. This paste-like substance was separated, dissolved in 450 g of cold water and 16.3 g of ammonium hexafluorophosphate dissolved in 200 g of water were dropped at 5° to 10° C. to liberate paste-like diazonium salt of hexafluorophosphoric acid. This paste-like substance was separated, kneaded in diisopropylether into a powder. The powder was filtered and vacuum dried. The yield was 23 g.

This compound is the multifunctional aromatic diazo compound of Formula (24) wherein $X^-$ is $PF_6^-$.

This compound belongs to the fifth type of aromatic diazo compound, a kind of compound of Formula (V').

2-Methoxyethanol solution of this compound had a $\lambda_{max}$ of UV spectrum of 382 nm, and an absorption coefficient of 27 where concentration is in g/liter and optical path length in cm. Solubility of this compound in 1-methoxy-2-propanol was no less than 25% at room temperature.

COMPARATIVE EXAMPLE 1

Synthesis of diphenylamine-4-diazonium salt/formaldehyde condensate

Diphenylamine-4-diazonium sulfate, 14.5 g (0.05 mole), was dissolved in 50 g of ice-cooled concentrated sulfuric acid and 1.2 g (0.04 mole) of paraformaldehyde were slowly added at 5° to 8° C., and agitated at 8° C. for 2 hours. This mixture was dropped into 200 g of ice-cooled isopropyl alcohol at about 5° C. The resulting precipitate was filtered, washed three times with cold isopropyl alcohol, and vacuum dried. The yield was 11 g.

COMPARATIVE EXAMPLE 2

Synthesis of 2-methoxy-4-hydroxy-5-benzoylbenzesulfonate of diphenylamine-4-diazonium salt/formaldehyde condensate Diphenylamine-4-diazonium salt/formaldehyde condensate synthesized in Comparative Example 1, 5 g, was dissolved in 60 g of ice-cooled 1.5% dilute sulfuric acid and 6 g of 2-methoxy-4-hydroxy-5-benzoylbenzenesulfonic acid dissolved in 40 g of cold water were poured under agitation. The resulting precipitate was filtered, washed three times with cold water, and vacuum dried. The yield was 7.5 g.

EXAMPLE 10

UV absorption spectrum of the diazo compounds according to the present invention Near-ultraviolet absorption spectra of the inventive aromatic diazo compounds are almost the same. UV absorption spectra of diazo compound (10) synthesized in Example 4 and the diphenylamine-4-diazonium salt/formaldehyde condensate synthesized in Comparative Example 1 in pH=3 aqueous solutions as representative examples were measured. The results are shown in FIG. 1. As can be seen from the figure, the diazo compound according to the present invention has a sharp absorption curve at $\lambda_{max}=374$ nm, whereas diphenylamine-4-diazonium salt/formaldehyde condensate has a broad absorption curve, and an absorption in the visible region at 420–500 nm.

EXAMPLE 11

Figure 2:
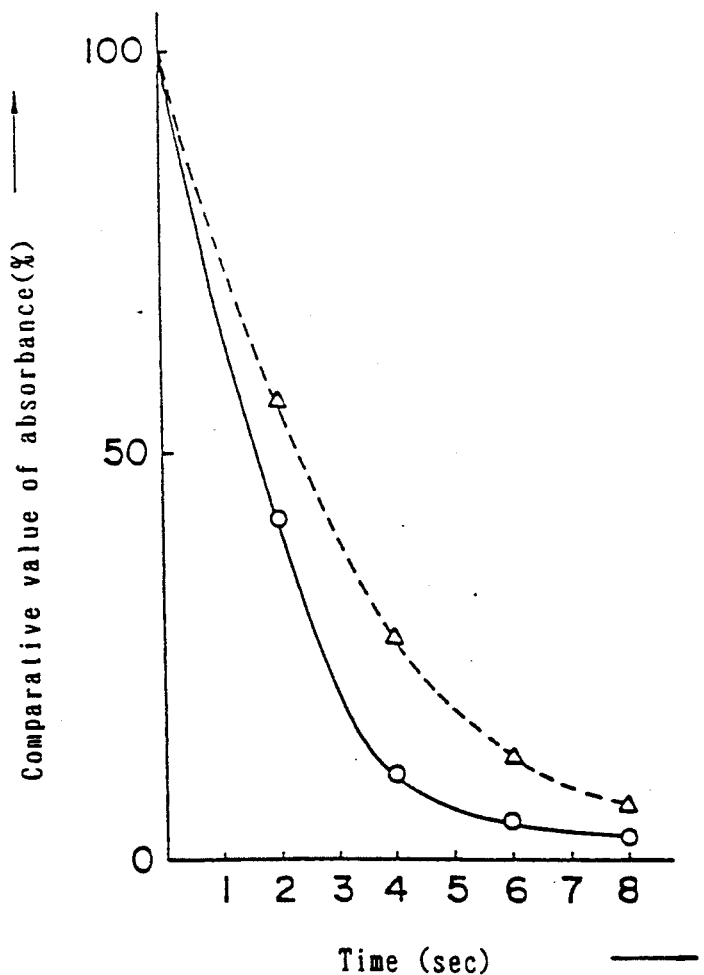
FIG. 2 is a graph showing changes in absorbance at $\lambda_{max}$, due to irradiation with light, of aqueous solution of pH=3 of diazo compound synthesized in Example 5 and diphenylamine-4-diazonium salt/formaldehyde condensate synthesized in Comparative Example 1.

Measurement of photodecomposition rate of diazo compound according to the present invention As a basic experiment of sensitivity to light of the inventive diazo compound, photodecomposition rates in aqueous solution were measured. Aqueous solutions of pH=3 (absorbance of 1 cm optical path length: 1.8) of aromatic diazo compound (19) synthesized in Example 5 and diphenylamine-4-diazonium salt/formaldehyde condensate synthesized in Comparative Example 1 were irradiated with an ultra-high pressure mercury lamp, and the absorbances of the solutions at $\lambda_{max}$ of UV absorption spectra measured. The results are shown in FIG. 2, wherein an unirradiated sample is assumed as 100%. It can be seen from the figure that the inventive diazo compound has a high sensitivity to light over the comparative sample.

EXAMPLE 12

Figure 3:
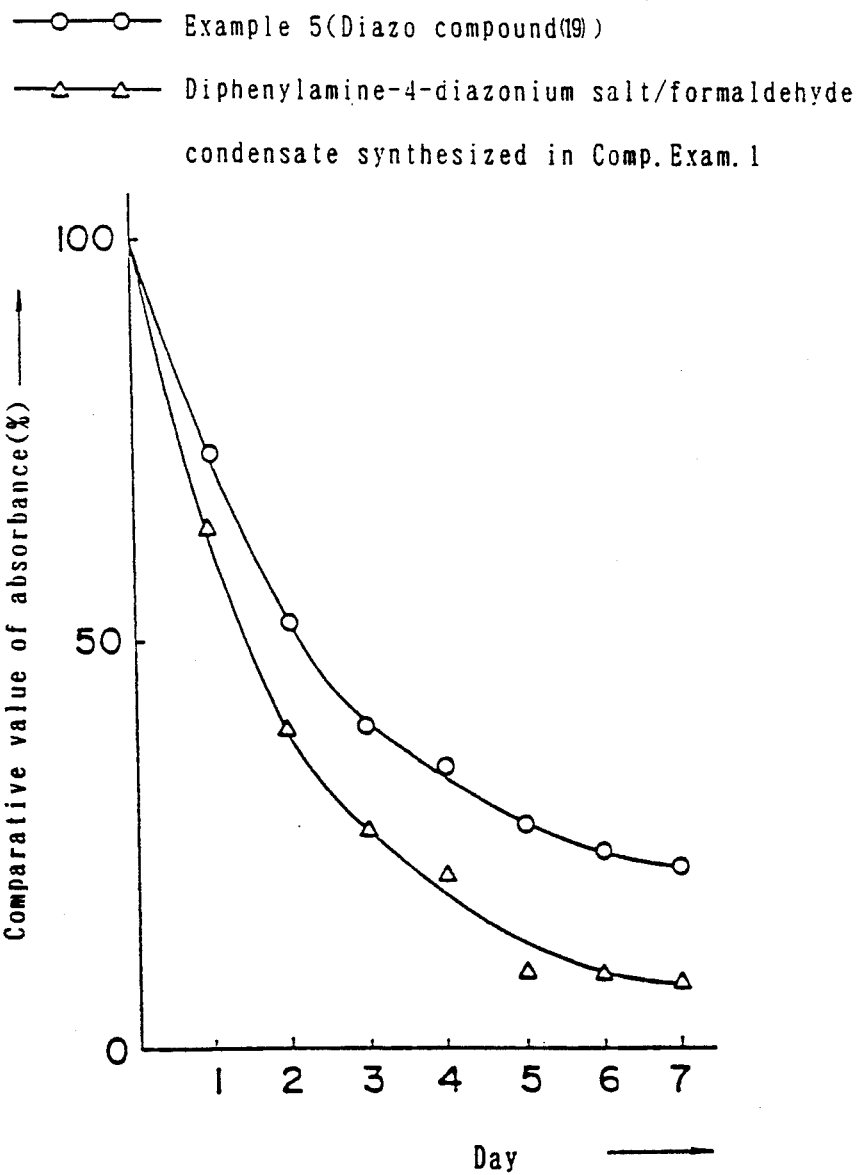
FIG. 3 is a graph showing changes in absorbance at $\lambda_{max}$, when stored at 55° C. under light-shielded condition, of aqueous solution of pH=3 of diazo compound synthesized in Example 5 and diphenylamine-4-diazonium salt/formaldehyde condensate synthesized in Comparative Example 1.

Measurement of storage stability of diazo compound according to the present invention As a basic experiment of storage stability of the inventive diazo compound, decomposition rate of the compound in aqueous solution was measured under light-shield condition. Aqueous solutions of pH=3 (absorbance of 1 cm optical path length; 2.0) of aromatic diazo compound (19) synthesized in Example 5 and diphenylamine-4-diazonium salt/formaldehyde condensate synthesized in Comparative Example 1 were stored in a constant-temperature tank at 55° C. under light-shielded condition, and the absorbances of the solutions at $\lambda_{max}$ of UV absorption spectra measured at every predetermined time. The results are shown in FIG. 3, wherein the initial absorbance is assumed as 100%. It can be seen from the figure that the inventive diazo compound is superior in storage stability to the comparative sample.

EXAMPLE 13

Photosensitive lithographic printing plate 1

Synthesis of copolymer (I)

In a 2,000-ml, 4-necked separable flask 300 g of methylcellosolve were placed and heated to 90° C. in a nitrogen stream. Into the flask was dropped a mixture of 162.3 g of acrylonitrile, 89.7 g of methylmethacrylate, 18.0 g of methacrylic acid, 30.0 g of glycerol-monomethacrylate, and 0.60 g of benzoylperoxide in 2 hours. After the completion of dropping, 300 g of methylcellosolve and 0.24 g of benzoylperoxide were dropped in over a period of 30 minutes, and reacted for 5 hours. After the completion of the reaction, the reaction mixture was diluted with 900.0 g of methylcellosolve. The reaction solution was poured into 15 liters of water to precipitate the copolymer. The precipitate was filtered, and vacuum dried at 80° C. to obtain copolymer (I).

A 0.24 mm thick aluminum plate was immersed for 3 minutes in a 10% trisodium phosphate aqueous solution maintained at 80° C. to degrease, surface grained with a Nylon brush, etched in sodium aluminate at 60° C. for 10 seconds, and desmatted in 3% sodium hydrogen sulfate aqueous solution. This aluminum plate was anodically oxidized in 20% sulfuric acid at 2 A/dm$^2$ for 2 minutes, and then treated in 2.5% sodium silicate aqueous solution at 70° C. for 1 minute to obtain an anodized aluminum plate.

This aluminum plate was applied with the following photosensitive solution (I) using a rotary coater. The plate was dried at 100° C. for 2 minutes.

| Composition of photosensitive solution (I) | |
|---|---|
| Diazo compound (11) (synthesized in Example 1) | 0.53 g |
| Copolymer (I) | 6.0 g |
| Oil Blue #603 (Orient Kagaku Kogyo) | 0.16 g |
| Phosphorous acid | 0.05 g |
| Methylcellosolove | 100 g |

The dry coating amount was 2.0 g/m$^2$. This photosensitive lithographic printing plate was exposed to a 1 kW metal halide lamp from a distance of 70 cm for 50 seconds. Developing solution DN-3C (Fuji Photo Film) was diluted (1:1) with water, and used to develop the photosensitive lithographic printing plate at 25° C. for 1 minute to obtain a lithographic printing plate.

This printing plate was used on the 3200 MCD Printing Press (Ryobi) to print high-grade paper to obtain more than 120,000 prints.

EXAMPLE 14

Photosensitive lithographic printing plate 2

An anodized aluminum plate was prepared using the same procedure as Example 13.

This aluminum plate was applied with the following photosensitive solution (2) using a rotary coater. The coated plate was dried at 100° C. for 2 minutes.

| Composition of photosensitive solution (2) | |
|---|---|
| Diazo compound (12) (synthesized in Example 2) | 1.09 g |
| Copolymer (I) | 6.0 g |
| Oil Blue #603 (Orient Kagaku Kogyo) | 0.16 g |
| Phosphorous acid | 0.16 g |
| Methylcellosolve | 100 g |

The dry coating amount was 2.0 g/m$^2$. This photosensitive lithographic printing plate was exposed to a 1 kW metal halide lamp from a distance of 70 cm for 65 seconds. Developing solution DN-3C (Fuji Photo Film) was diluted (1:1) with water, and used to develop the photosensitive lithographic printing plate at 25° C. for 1 minute to obtain a lithographic printing plate.

This printing plate was used on the 3200 MCD Printing Press (Ryobi) to print high-grade paper to obtain more than 120,000 prints.

EXAMPLE 15

Photosensitive lithographic printing plate 3

An anodized aluminum plate was prepared using the same procedure as Example 13.

This aluminum plate was applied with the following photosensitive solution (3) using a rotary coater. The coated plate was dried at 100° C. for 2 minutes.

| Composition of photosensitive solution (3) | |
|---|---|
| Diazo compound (17) (synthesized in Example 3) | 0.69 g |
| Copolymer (I) | 6.0 g |
| Oil Blue #603 (Orient Kagaku Kogyo) | 0.16 g |
| Phosphorous acid | 0.15 g |
| Methylcellosolve | 100 g |

The dry coating amount was 2.0 g/m$^2$. This photosensitive lithographic printing plate was exposed to a 1 kW metal halide lamp from a distance of 70 cm for 65 seconds. Developing solution DN-3C (Fuji Photo Film) was diluted (1:1) with water, and used to develop the photosensitive lithographic printing plate at 25° C. for 1 minute to obtain a lithographic printing plate.

This printing plate was used on the 3200 MCD Printing Press (Ryobi) to print high-grade paper to obtain more than 120,000 prints.

COMPARATIVE EXAMPLE 3

Comparative sample of photosensitive lithographic printing plate

An anodized aluminum plate was prepared using the same procedure as Example 13.

This aluminum plate was applied with the following comparative photosensitive solution (1) using a rotary coater. The coated plate was dried at 100° C. for 2 minutes. Composition of comparative photosensitive solution (1)

| Comparative diazo compound (2) | |
| --- | --- |
| 2-methoxy-4-hydroxy-5-benzoylbenzene sulfonate salt of diphenylamine-4-diazonium salt-formaldehyde condensate | 0.51 g |
| Copolymer (I) | 6.0 g |
| Oil Blue #603 (Orient Kagaku Kogyo) | 0.16 g |
| Phosphorous acid | 0.05 g |
| Methylcellosolve | 100 g |

The dry coating amount was 2.0 g/m². This photosensitive lithographic printing plate was exposed to a 1 kW metal halide lamp from a distance of 70 cm for 90 seconds. Developing solution DN-3C (Fuji Photo Film) was diluted (1:1) with water, and used to develop the photosensitive lithographic printing plate at 25° C. for 1 minute to obtain a lithographic printing plate.

This printing plate was used on the 3200 MCD Printing Press (Ryobi) to print high-grade paper to obtain more than 100,000 prints.

The photosensitive lithographic printing plates prepared in Examples 13, 14, and 15 and the comparative sample prepared in Comparative Example 3 exposed by using Kodak Photographic step tablet No.2 to obtain overall black at step-5 required exposure times as shown in Table 1. As can be seen from the table, the inventive photosensitive lithographic printing plates 1 to 3 are higher in sensitivity than the comparative sample.

| Photosensitive lithographic printing plate | Diazo compound used | Exposure time |
| --- | --- | --- |
| Example 13 | Compound (11) | 50 sec |
| Example 14 | Compound (12) | 65 sec |
| Example 15 | Compound (17) | 65 sec |
| Comparative sample | Comparative compound (2) | 90 sec |

As shown in the table, the photosensitive composition according to the present invention is highly photosensitive, and can be developed rapidly with a weak alkaline developing solution, providing a lithographic printing plate which is good in ink-receptivity, highly resistant to printing and superior in storage stability.

EXAMPLE 16

Photosensitive screen printing plate

| Composition of photosensitive solution (4) | |
| --- | --- |
| Diazo compound (19) (synthesized in Example 5) | 0.35 g |
| Water | 4.65 g |
| Direct Photo-emulsion | |
| Diazo Type SP-1700H (Murakami Screen) | 45.00 g |

Photosensitive solution (4) of the above composition was coated on a 250-mesh monofilament polyester screen extended on an aluminum frame with a bucket. Coating and air drying at 40° C. for 10 minutes were repeated 4 to 5 times to form a photosensitive film with a thickness of 70 μm (including the screen thickness).

This screen photosensitive plate was exposed with a 4 kW ultra-high pressure mercury lamp (Oak Seisakusho) from a distance of 1 m for 2 minutes. Development was performed as follows:

This screen photosensitive plate was immersed in water at 25° C. for 1 minute to dissolve out unexposed portions, and sprayed with 20° C. water at a pressure of 6 kg/cm² with a spray gun from a distance of 30 cm to completely remove residual photosensitive film of the pattern portion.

Using the diphenylamine-4-diazonium salt/formaldehyde condensate synthesized in Comparative Example 1, a comparative sample of photosensitive screen printing plate was prepared using the same procedure as above.

Both plates were compared. As a result, the plate using the diazo compound (19) of the present invention was higher in photosensitivity and superior in water and solvent resistance. Printing was carried out using the plate. No damage to the pattern was noted, and printing was carried out with consistent printing reproducibility.

EXAMPLE 17

Colored image formation type photosensitive material

Photosensitive film to obtain colored image

| Composition of intermediate layer formation solution | |
| --- | --- |
| Vinylchloride-vinylidenechloride copolymer (40% solution) (Kureha Kagaku, Kurehalon SOA) | 10.00 g |
| Toluene | 45.00 g |
| Ethyl acetate | 45.00 g |
| Composition of colored layer formation solution | |
| Diazo compound (10) 10% aqueous solution (synthesized in Example 4) | 9.00 g |
| Polyvinylalcohol (average polymerization degree: 1700, 88% hydrolysis) | 100.00 g |
| Pigment dispersion (Phthalocyanine Blue 20% solution) | 4.00 g |
| Water | 100.00 g |
| Isopropyl alcohol | 10.00 g |

The above intermediate layer formation solution was coated on one side of a 100 μm thick biaxially oriented polyethyleneterephthalate film with a bar coater, and dried at 100° C. for 1 minute to form an intermediate layer of approximately 1 μm in thickness.

On top of the intermediate layer, the colored layer formation solution was coated with a bar coater so that the coating film thickness after drying is 3 μm, and dried in a 80° C. air dryer for 1 minute to obtain a cyan-colored film-I.

The colored photosensitive surface of the film-I was contacted with a negative original (color-divided network negative-for cyan-colored plate), and exposed with a 1-kW metal halide lamp from a distance of 70 cm for 2 minutes. The non-image portion was washed out by spraying water at room temperature from a nozzle under a pressure of 1 kg/cm², water removed, and hot air dried at 50° C. to obtain a cyan-colored positive image.

The cyan-colored positive image of the diazo compound according to the present invention exhibited pure tints of the coloring agent, because residual substance after photodegradation is less colored compared to that obtained using another diazo compound (diphenylamine-4-diazonium salt/formaldehyde condensate).

EXAMPLE 18

Basic experiments for the identification of the chemical structure of the aromatic diazo compounds according to the present invention As described above, an industrial grade of the polyglycidyl compound, which is an important raw material of the aromatic diazo compound according to the present invention, is a mixture, and it is difficult to obtain a pure, single compound. Therefore, the aromatic diazo compound according to the present invention is obtained as a mixture. Furthermore, aromatic diazo compounds of Formula (IV) described in Claim 4, that of Formula (V) described in Claim 5, and that of Formula (V') belonging to Claim 6 are mixtures of lower polycondensates with different molecular weights, similar to oligomers of polymer compounds produced by polycondensation reactions. Thus, the aromatic diazo compounds according to the present invention are those compounds having at least two groups of Formula (I) in the molecule, and are not single compounds except for specific cases, but are agglomerates of molecules with different molecular weights. Therefore, it is difficult to identify the chemical structure of each of the aromatic diazo compounds like a single compound.

However, since the means to introduce at least two groups of Formula (I) into the molecule is a known reaction, the chemical structure of the diazo compound according to the present invention can be identified when the chemical structure of the group of Formula (I) can be identified. Then, in these experiments, a compound of Formula (69) was synthesized as a model compound of the group of Formula (I).

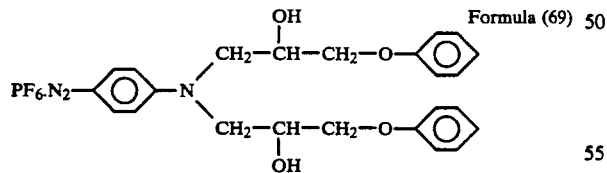

Formula (69)

The compound of Formula (69) is a compound corresponding to the following Formula (Z) in Formula (I).
Formula (Z)

$X^-$ is $PF_6^-$ or $R^1 = R^2 = H$,

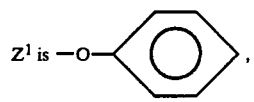

$R^3$ is 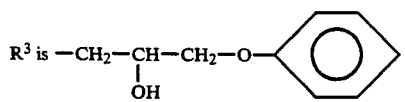

The compound of Formula (69) was synthesized using the same procedure as described in Examples 1, 2, 3, and 5. p-aminoacetanilide and glycidylphenylether were reacted to obtain the compound of Formula (70), which was deacetylated, diazotized, and reacted with NH₄PF₆ to yield the objective compound of Formula (69).

This synthesis process is shown below:

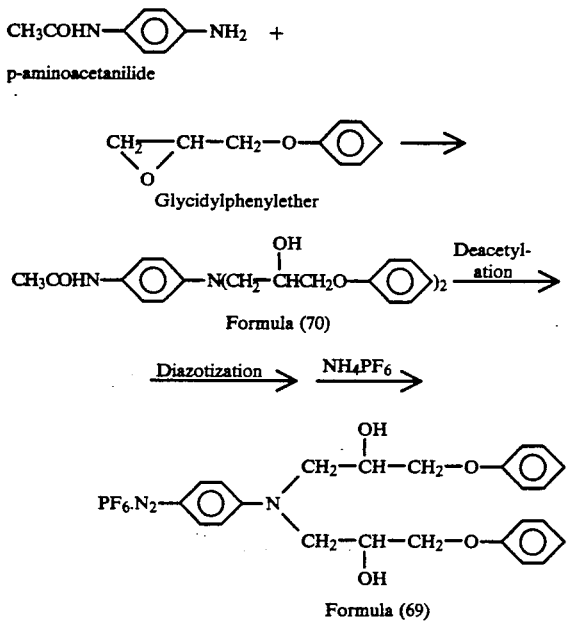

In the above synthesis process, Formula (70) is an important intermediate compound, and its chemical structure was also identified.

Compounds of known chemical structures of Formulae (71) to (73) were also synthesized, which were used as reference samples for the identification of the structures of the compounds of Formulae (69) and (70).

Synthesis of compound of Formula (70)

p-Aminoacetanilide, 0.1 mole, was dissolved in 60 g of acetic acid, and 0.21 mole of glycidylphenylether were added at 25° to 30° C. to react both reagents under the same condition as in Example 1. The reaction mixture was dropped under agitation in a solution of 65 g sodium carbonate dissolved in 1 kg water, separating an oil-like layer.

This oil-like substance was extracted with methylene chloride and the methylene chloride extract was washed by shaking with water, dehydrated with magnesium sulfate powder for dehydration, and methylene chloride removed by distillation to obtain 39.5 g of raw crystal of the compound of Formula (70).

This crystal was mixed with 300 g of benzene, heated and refluxed with a Dean-Stark trap to dehydrate. 100 g of benzene were removed by distillation and the remaining solution was cooled to 40° C., mixed with 80 g of methylene chloride, and gradually cooled under stirring to deposit web-like crystal. This crystal was filtered, washed 3 times with benzene, and allowed to stand under vacuum to obtain 35.5 g of crystal.

This crystal was dried in a vacuum drier at 75° C. for 5 hours to obtain a white powder with a melting point of 88° to 98° C. Since the compound of Formula (70) has two asymmetric carbon atoms with OH groups, the compound of Formula (70) is a mixture of three stereoisomers of SS, RR, and SR in the arrangement of asymmetric carbon atoms. The compound of formula (70) synthesized in this experiments is also a mixture like this, and thus shows an indefinite melting point.

Synthesis of compound of Formula (69)

Crystal of the compound of Formula (70), 22.5 g (0.05 mole), obtained above was dissolved in 30 g acetic acid and 24 g of 35% hydrochloric acid were added. The product was deacetylated and diazotized as in Example 3, and the resulting diazo compound was reacted with $NH_4PF_6$ aqueous solution to obtain 19.0 g a $PF_6^-$ salt of diazo compound.

The diazo compound was dissolved in a mixture of 20 g acetone and 15 g chloroform, filtered. The filtrate was mixed with 50 g of chloroform, allowed to stand in a dark, cool place. The deposited diazonium salt crystal was filtered, washed twice with small amounts of chloroform, and allowed to stand in a dark, cool place under vacuum to obtain 12 g of light yellow crystal of the objective compound.

Synthesis of compounds of Formulae (71) to (73)

p-Diethylaminobenzene-diazonium sulfate was dissolved in water and insolubles were removed by filtration. The filtrate was dropped into $NH_4PF_6$ aqueous solution and the resulting crystal filtered, dissolved in about the same weight of acetone, insolubles filtered. The filtrate was mixed with twice the amount of chloroform, and allowed to stand in a cool, dark place to obtain a crystal of the compound of Formula (71).

Using p-phenylaminobenzene-diazonium sulfate, the same procedure was used to obtain a crystal of the compound of Formula (73).

N,N-diethylamino-p-phenylenediamine was acetylated with acetic anhydride in tetrahydrofuran, poured into water, neutralized with sodium carbonate, and cooled with ice to obtain a crystal of the compound of Formula (72).

Structure identification of compounds of Formulae (70) and (69)

(a) Structure identification by way of proton NMR spectrum

Figure 5:
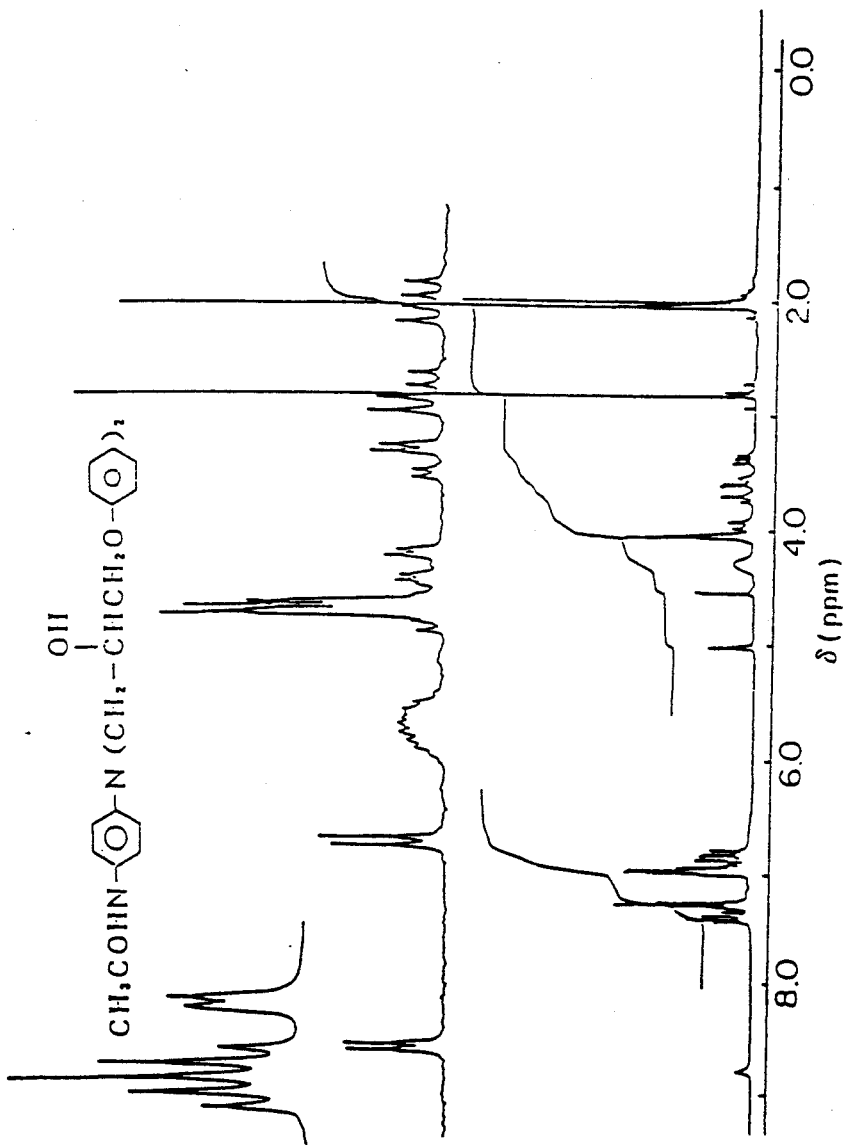
FIG. 5 is a $^1$H NMR (270 MHz acetone-$d_6$, TMS) spectrum of a compound of Formula (70).
Figure 6:
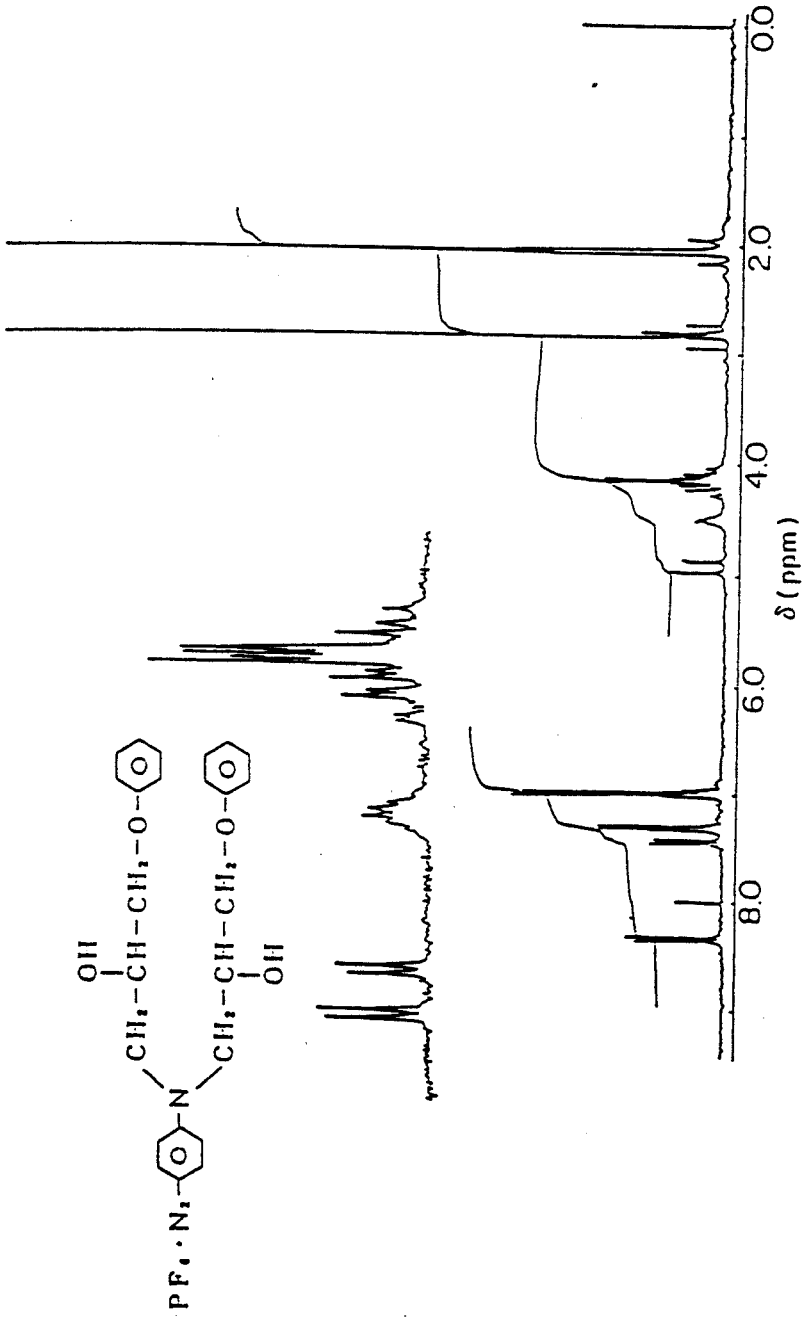
FIG. 6 is a $^1$H NMR (270 MHz acetone-$d_6$, TMS) spectrum of a compound of Formula (69).
Figure 7:
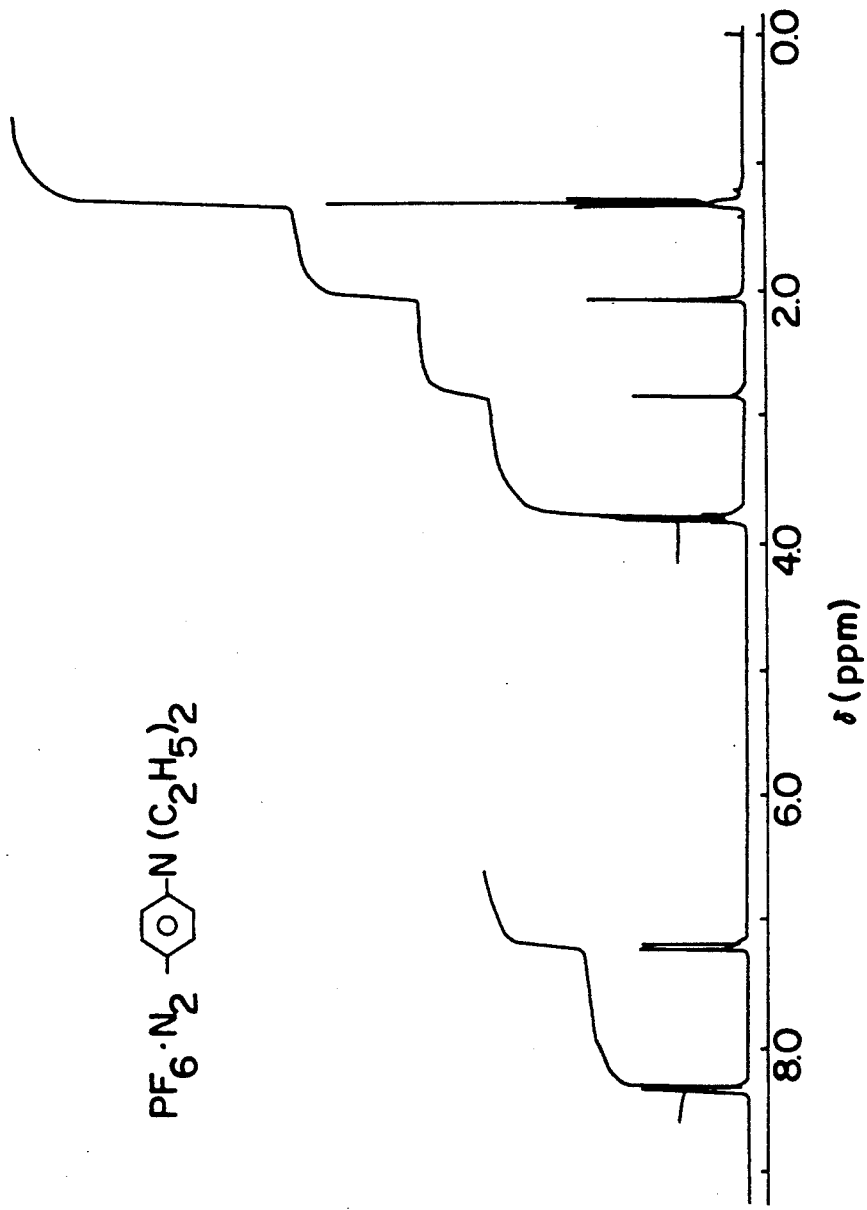
FIG. 7 is a $^1$H NMR (270 MHz acetone-$d_6$, TMS) spectrum of a compound of Formula (71).
Figure 8:
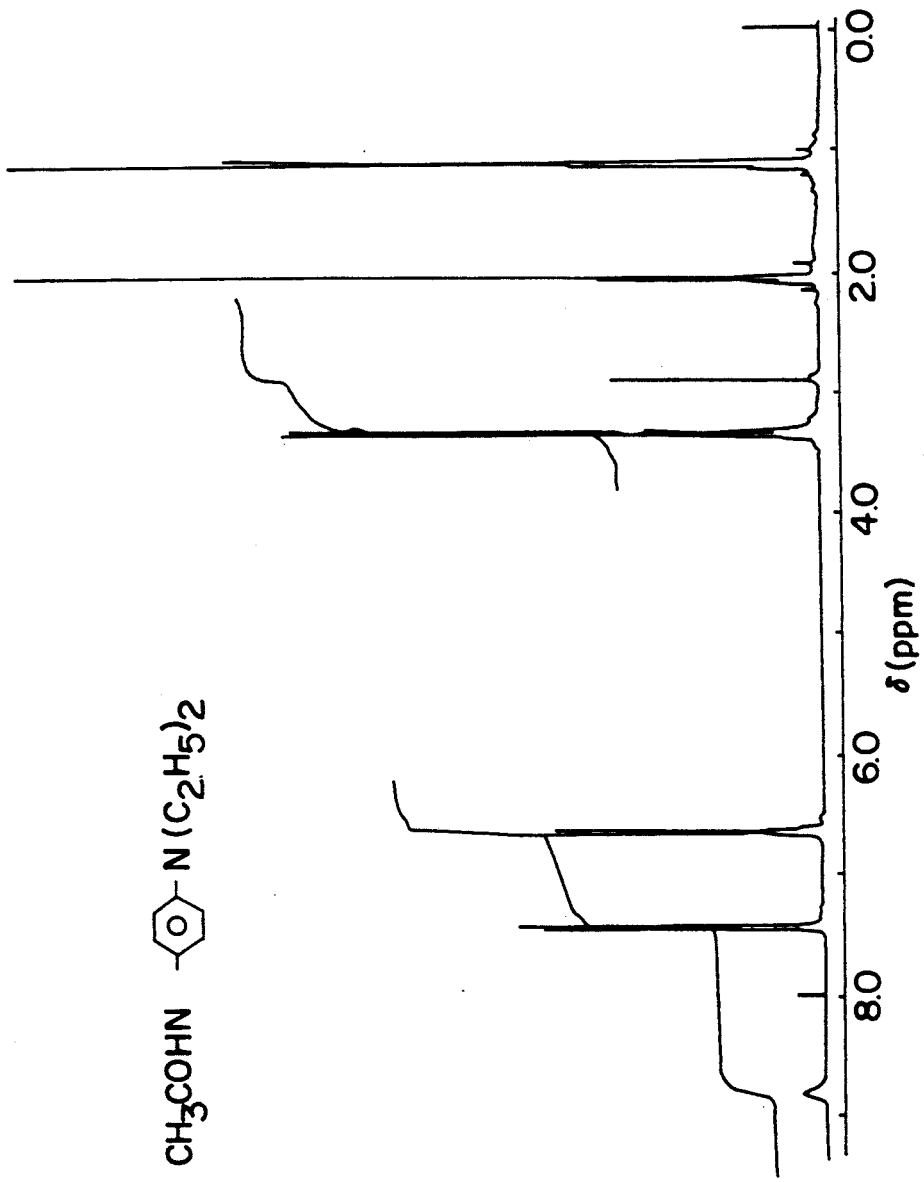
FIG. 8 is a $^1$H NMR (270 MHz acetone-$d_6$, TMS) spectrum of a compound of Formula (72).

Using a proton NMR spectrometer with an electromagnetic wave frequency of 270 MHz, compounds of Formulae (69) to (72) were dissolved in acetone-$d_6$ and measured for NMR spectra. $^1H$ NMR spectra of the compounds of Formulae (70) and (69) are shown in FIG. 5 and FIG. 6, respectively, and the following Table 2 and Table 3 show analytical data thereof. Spectra of the compounds of known structures of Formulae (71) and (72) are shown in FIG. 7 and FIG. 8.

TABLE 2

| Analytical result of Formula (70) | | | |
|---|---|---|---|
| TOTAL | 84 | | |
| RESOL | 3295 | −4 HZ | |
| EXREF | 0.0000 PPM | | |
| OBS | 1211.2426 HZ | | |
| NGAIN | 3 | | |
| NO | FREQ(Hz) | PPM | INT % |
| 1 | 2375.02 | 8.805 | 233 |
| 2 | 2374.03 | 8.801 | 216 |
| 3 | 2010.16 | 7.452 | 528 |
| 4 | 2002.25 | 7.423 | 879 |
| 5 | 1993.02 | 7.388 | 676 |
| 6 | 1983.80 | 7.354 | 441 |
| 7 | 1974.57 | 7.320 | 761 |
| 8 | 1972.59 | 7.313 | 1004 |
| 9 | 1970.61 | 7.305 | 362 |
| 10 | 1967.32 | 7.293 | 1223 |
| 11 | 1965.34 | 7.286 | 1748 |
| 12 | 1963.69 | 7.280 | 1229 |
| 13 | 1969.72 | 7.269 | 513 |
| 14 | 1958.42 | 7.268 | 1242 |
| 15 | 1956.44 | 7.253 | 1137 |
| 16 | 1954.13 | 7.244 | 206 |
| 17 | 1935.35 | 7.175 | 103 |
| 18 | 1889.53 | 7.005 | 996 |
| 19 | 1888.22 | 7.000 | 1381 |
| 20 | 1885.53 | 6.990 | 1220 |
| 21 | 1884.59 | 6.986 | 1646 |
| 22 | 1881.62 | 6.975 | 822 |
| 23 | 1880.63 | 6.972 | 1218 |
| 24 | 1879.65 | 6.968 | 1189 |
| 25 | 1878.00 | 6.962 | 1270 |
| 26 | 1876.60 | 6.957 | 1605 |
| 27 | 1870.42 | 6.934 | 1003 |
| 28 | 1869.10 | 8.929 | 989 |
| 29 | 1862.84 | 6.906 | 455 |
| 30 | 1851.63 | 6.864 | 754 |
| 31 | 1849.65 | 6.857 | 310 |
| 32 | 1842.48 | 6.830 | 701 |
| 33 | 1837.79 | 6.813 | 660 |
| 34 | 1828.56 | 6.779 | 565 |
| 35 | 1358.56 | 5.036 | 615 |
| 36 | 1354.61 | 5.022 | 637 |
| 37 | 1232.64 | 4.569 | 725 |
| 38 | 1227.72 | 4.551 | 801 |
| 39 | 1178.78 | 4.340 | 278 |
| 40 | 1165.75 | 4.321 | 312 |
| 41 | 1161.14 | 4.304 | 322 |
| 42 | 1107.42 | 4.105 | 215 |
| 43 | 1102.47 | 4.007 | 263 |
| 44 | 1097.86 | 4.070 | 1785 |
| 45 | 1096.21 | 4.064 | 1531 |
| 46 | 1092.59 | 4.050 | 1633 |
| 47 | 1090.61 | 4.043 | 1260 |
| 48 | 1077.75 | 3.995 | 347 |
| 49 | 1074.46 | 3.983 | 322 |
| 50 | 1062.56 | 3.939 | 410 |
| 51 | 1059.38 | 3.927 | 336 |
| 52 | 1016.78 | 3.769 | 247 |
| 53 | 1012.50 | 3.753 | 249 |
| 54 | 1001.62 | 3.713 | 499 |
| 55 | 997.33 | 3.697 | 443 |
| 56 | 977.56 | 3.624 | 516 |
| 57 | 969.98 | 3.596 | 472 |
| 58 | 962.40 | 3.567 | 277 |
| 59 | 955.15 | 3.541 | 266 |
| 60 | 925.40 | 3.431 | 354 |
| 61 | 917.24 | 3.400 | 327 |
| 62 | 910.32 | 3.374 | 315 |
| 63 | 902.08 | 3.344 | 293 |

TABLE 2-continued

Analytical result of Formula (70)
TOTAL 84
RESOL 3295 −4 HZ
EXREF 0.0000 PPM
OBS 1211.2426 HZ
NGAIN 3

| NO | FREQ(Hz) | PPM | INT % |
|---|---|---|---|
| 64 | 792.33 | 2.937 | 205 |
| 65 | 763.90 | 2.832 | 8322 |
| 66 | 755.74 | 2.801 | 395 |
| 67 | 754.76 | 2.798 | 466 |
| 68 | 753.77 | 2.794 | 382 |
| 69 | 735.64 | 2.727 | 224 |
| 70 | 584.03 | 2.163 | 147 |
| 71 | 582.05 | 2.157 | 198 |
| 72 | 579.74 | 2.149 | 149 |
| 73 | 557.99 | 2.068 | 2733 |
| 74 | 556.01 | 2.061 | 4556 |
| 75 | 553.71 | 2.052 | 7769 |
| 76 | 551.40 | 2.044 | 5325 |
| 77 | 549.09 | 2.035 | 2301 |
| 78 | 542.03 | 2.012 | 3140 |
| 79 | 541.51 | 2.007 | 3594 |
| 80 | 527.67 | 1.956 | 263 |
| 81 | 525.36 | 1.947 | 286 |
| 82 | 523.05 | 1.939 | 200 |
| 83 | 513.17 | 1.902 | 174 |
| 84 | 492.40 | 1.825 | 100 |

TABLE 3

Analytical result of Formula (69)
TOTAL 77
RESOL 3295 −4 HZ
EXREF 0.0000 PPM
OBS 1211.5722 HZ
NGAIN 3

| NO | FREQ(Hz) | PPM | INT % |
|---|---|---|---|
| 1 | 2255.05 | 8.368 | 576 |
| 2 | 2253.40 | 8.354 | 182 |
| 3 | 2245.49 | 8.324 | 630 |
| 4 | 2158.81 | 8.003 | 320 |
| 5 | 2010.82 | 7.454 | 384 |
| 6 | 2009.58 | 7.449 | 405 |
| 7 | 2007.53 | 7.442 | 134 |
| 8 | 2000.93 | 7.418 | 382 |
| 9 | 1999.62 | 7.413 | 455 |
| 10 | 1977.86 | 7.332 | 496 |
| 11 | 1975.56 | 7.324 | 194 |
| 12 | 1973.58 | 7.316 | 130 |
| 13 | 1970.61 | 7.305 | 811 |
| 14 | 1968.64 | 7.298 | 816 |
| 15 | 1966.66 | 7.291 | 173 |
| 16 | 1964.02 | 7.281 | 281 |
| 17 | 1961.71 | 7.272 | 822 |
| 18 | 1959.08 | 7.263 | 115 |
| 19 | 1886.57 | 6.994 | 1374 |
| 20 | 1882.61 | 6.979 | 146 |
| 21 | 1878.99 | 6.966 | 1291 |
| 22 | 1878.33 | 6.963 | 1245 |
| 23 | 1872.07 | 6.948 | 238 |
| 24 | 1871.08 | 6.936 | 286 |
| 25 | 1870.09 | 6.933 | 129 |
| 26 | 1858.88 | 6.891 | 78 |
| 27 | 1348.77 | 4.970 | 332 |
| 28 | 1335.82 | 4.952 | 359 |
| 29 | 1131.74 | 4.870 | 264 |
| 30 | 1308.80 | 4.852 | 297 |
| 31 | 1223.10 | 4.534 | 85 |
| 32 | 1214.53 | 4.502 | 218 |
| 33 | 1211.24 | 4.490 | 155 |
| 34 | 1209.92 | 4.485 | 199 |
| 35 | 1205.96 | 4.478 | 143 |
| 36 | 1154.88 | 4.281 | 114 |
| 37 | 1151.25 | 4.268 | 119 |
| 38 | 1144.00 | 4.241 | 81 |
| 39 | 1139.72 | 4.225 | 285 |
| 40 | 1136.09 | 4.211 | 211 |
| 41 | 1128.84 | 4.185 | 322 |
| 42 | 1124.56 | 4.169 | 215 |

TABLE 3-continued

Analytical result of Formula (69)
TOTAL 77
RESOL 3295 −4 HZ
EXREF 0.0000 PPM
OBS 1211.5722 HZ
NGAIN 3

| NO | FREQ(Hz) | PPM | INT % |
|---|---|---|---|
| 43 | 1122.25 | 4.160 | 122 |
| 44 | 1118.95 | 4.148 | 907 |
| 45 | 1116.32 | 4.138 | 643 |
| 46 | 1114.01 | 4.130 | 796 |
| 47 | 1110.71 | 4.117 | 802 |
| 48 | 1104.78 | 4.095 | 136 |
| 49 | 1101.48 | 4.083 | 306 |
| 50 | 1095.55 | 4.061 | 178 |
| 51 | 1088.96 | 4.037 | 79 |
| 52 | 1086.65 | 4.028 | 157 |
| 53 | 792.00 | 2.936 | 288 |
| 54 | 763.98 | 2.832 | 10286 |
| 55 | 755.09 | 2.799 | 568 |
| 56 | 735.97 | 2.728 | 274 |
| 57 | 584.36 | 2.166 | 164 |
| 58 | 582.05 | 2.157 | 219 |
| 59 | 580.07 | 2.150 | 125 |
| 60 | 577.77 | 2.142 | 84 |
| 61 | 563.92 | 2.090 | 122 |
| 62 | 558.32 | 2.069 | 2736 |
| 63 | 556.34 | 2.062 | 5045 |
| 64 | 554.04 | 2.054 | 8327 |
| 65 | 551.73 | 2.045 | 5442 |
| 66 | 549.75 | 2.038 | 2434 |
| 67 | 547.11 | 2.028 | 165 |
| 68 | 544.15 | 2.017 | 100 |
| 69 | 541.51 | 2.007 | 82 |
| 70 | 534.26 | 1.980 | 85 |
| 71 | 532.61 | 1.974 | 106 |
| 72 | 530.31 | 1.966 | 145 |
| 73 | 528.33 | 1.958 | 230 |
| 74 | 526.35 | 1.951 | 289 |
| 75 | 524.04 | 1.942 | 200 |
| 76 | 521.74 | 1.934 | 125 |
| 77 | 0.00 | 0.000 | 961 |

In FIG. 5, the upper spectrum curve is an enlargement of the portion of δ between 2.0 and 2.1, and the middle spectrum curve is an enlargement of the portion of δ between 3.3 and 5.4. The five peaks in the region of δ between 2.035 and 2.068 are $^1H$ which is not substituted with D, remaining in acetone—$d_6$ solvent, and the spectrum in the portion of δ between 2.7 and 2.9 is due to $H_2O$ dissolved in acetone—$d_6$.

It has been found that all spectra in FIG. 5, except those shown above, completely belong to all of H of Formula (70), as described below, and thus the correctness of Formula (70) has been confirmed.

Formula (70) has two asymmetric carbon atoms to which OH groups are attached. Therefore, molecules represented by Formula (70) include three stereoisomers, which configurations are SS, RR, and SR. Isomers of SS and RR differ only in optical rotation, and other properties are the same including NMR.

On the other hand, the isomer SR differs from the above two isomers in various properties including NMR. Thus, NMR should identify the compound of Formula (70) as two isomers. Contribution of the spectrum shown in Table 4 below expressly shows this fact.

TABLE 4

Formula (70)

$^1H$ NMR (270MHz, acetone - $d_6$, TMS) to a mixture of two stereoisomers (1:1)
δ(ppm)
2.00(s) and 2.01(s) (totally 3H, C$\underline{H}_3$CONH—).

TABLE 4-continued

Formula (70)

3.39(dd, $J=15.2$, 8.2Hz) and 3.58(dd, $J=15.2$, 7.4 Hz)
(totally 2H, >NC$\underline{H}_a H_b$—), 3.73(dd, $J=15.2$, 4.3Hz) and
3.96(dd, $J=15.2$, 3.3Hz) (totally 2H, >NCH$_a\underline{H}_b$—),
4.0–4.1(m, 4H, —CH$_2$OPh),
4.2–4.4(m, 2H, —C$\underline{H}$(OH)—),
4.56(d, $J=5.1$Hz) and 5.03(d, $J=4.0$Hz)
(totally 2H, disappeared in acetone-d$_6$-D$_2$O, O$\underline{H}$),
6.79(d, $J=9.2$Hz) (totally 2H, Ar$\underline{H}$),
6.9–7.05(m, 6H, Ar$\underline{H}$), 7.25–7.35(m, 4H, Ar$\underline{H}$), 7.40(d,
$J=9.2$Hz) and 7.44(d, $J=9.2$Hz) (totally 2H, Ar$\underline{H}$),
8.80(broad s, 1H, disappeared in acetone-d$_6$-D$_2$O, —CON$\underline{H}$—).

In FIG. 6, the upper spectrum curve is an enlargement of the portion of δ between 3.8 and 5.2. The spectrum in the portion of δ between 1.9 and 2.1 and that between 2.7 and 2.9 are individually from H and H$_2$O present in acetone-d$_6$, and the spectrum of δ=8 is due to careless contamination coming with TMS. Contribution of the spectrum is as shown below, which corresponds to all H in Formula (69).

TABLE 5

Formula (69)

$^1$H NMR (270MHz, acetone - d$_6$, TMS) to a mixture of two stereo isomers (1:1)
δ(ppm)
4.03–4.28(m, 8H, >N—CH$_2$—, C$\underline{H}_2$OP$_n$),
4.47–4.53(m, 2H, —C$\underline{H}$(OH)—),
4.86(d, $J=4.9$Hz) and 4.96(d, $J=5.0$Hz) (totally 2H,
acetone-d$_6$-D$_2$O, O$\underline{H}$),
6.96–6.99(m, 6H, Ar$\underline{H}$), 7.26–7.33(m, 4H, Ar$\underline{H}$), 7.43(d,
$J=9.9$Hz) and 7.44(d, $J=9.9$Hz) (totally 2H, Ar$\underline{H}$),
8.34(d, $J=9.6$Hz) and 8.35(d, $J=9.6$Hz) (totally 2H, Ar$\underline{H}$)

FIG. 7 and FIG. 8 are $^1$H NMR (acetone-d$_6$, TMS) of Formulae (71) and (72) which have known structures. Similarly to FIG. 5–FIG. 6, spectra of H and H$_2$O remaining in acetone-d$_6$ individually appear in portion of δ of 2.05–2.13 and 2.84–2.89, and a spectrum due to contamination appears at 8.0. Contributions of the individual spectra are shown in Table 6 and Table 7.

TABLE 6

Formula (71)

δ(ppm)
1.29–1.34(t, $J=7.3$Hz, 6H, —CH$_2$C$\underline{H}_3$),
3.75–3.83(q, $J=7.3$Hz, 4H, >N—CH$_2$—),
7.29(d, $J=9.9$Hz, 2H, Ar$\underline{H}$),
8.33(d, $J=9.9$Hz, 2H, Ar$\underline{H}$),

TABLE 7

Formula (72)

δ(ppm)
1.08–1.13(t, $J=6.9$Hz, 6H, —CH$_2$C$\underline{H}_3$),
2.20(S, 3H, C$\underline{H}_3$CO—),
3.29–3.36(q, $J=6.9$Hz, 4H, >N—C$\underline{H}_2$—),
6.63(d, $J=9.2$Hz, 2H, Ar$\underline{H}$),
7.40(d, $J=9.2$Hz, 2H, Ar$\underline{H}$),
8.81(broad S, 1H, disappeared in acetone-d$_6$-D$_2$O, —CON$\underline{H}$—)

Characteristic changes among the effects on NMR of other H when CH$_3$CONH- of Formula (72) of known structure is substituted with PF$_6$N$_2$- to convert it into a compound of Formula (71) are the two points shown in Table 8 shown below:

TABLE 8

(i) NMR of methylene proton (>N—CH$_2$—) bonded to nitrogen atom is shifted by about 0.47 ppm to lower magnetic field.

TABLE 8-continued (ii) NMR of aromatic ring protons at both ortho positions to which CH$_3$CONH are bonded are shifted by 0.93 ppm to lower magnetic field.

Similarly, NMR of the compounds of Formulae (70) and (69) are compared in Table 9 below:

TABLE 9

(i) NMR of methylene proton (>N—CH$_2$—) bonded to nitrogen atom is shifted by an average of 0.48 ppm to lower magnetic field.
(ii) NMR of aromatic ring protons at both ortho positions to which CH$_3$CONH— are bonded are shifted by 0.92 ppm to lower magnetic field.

As described above, the fact that the chemical shift of NMR when Formula (70) is changed to Formula (69) is similar to the chemical shift of NMR when Formula (72) of known structure is changed to Formula (71) is a proof of the fact that Formulae (70) and (69) are correct.

Although formation of Formula (70') corresponding to an isomer of Formula (70) can be considered, there is a result of study that a compound of Formula (70') is hard to be formed, which has already been described above.

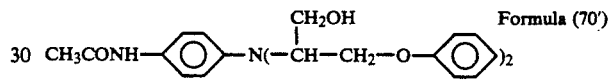

Formula (70')

Formula (70) is a secondary alcohol, whereas Formula (70') is a primary alcohol. It has been reported that when an alcohol is dissolved in acetone-d$_6$ and measured for NMR, NMR of H of OH group appears as a triplet for primary alcohol and as a doublet for secondary alcohol (D. J. Plasto, C. R. Johnson, *Organic Structure Determination*, Prentice-Hall, Englewood Cliffs, N.J.(1969)). As can be seen from FIG. 5 and FIG. 6, in NMR spectra of the compounds of Formulae (70) and (69), H of OH group appears as a doublet. Therefore, both of the compounds are secondary alcohols, rather than primary alcohols of Formula (70').

Figure 9:
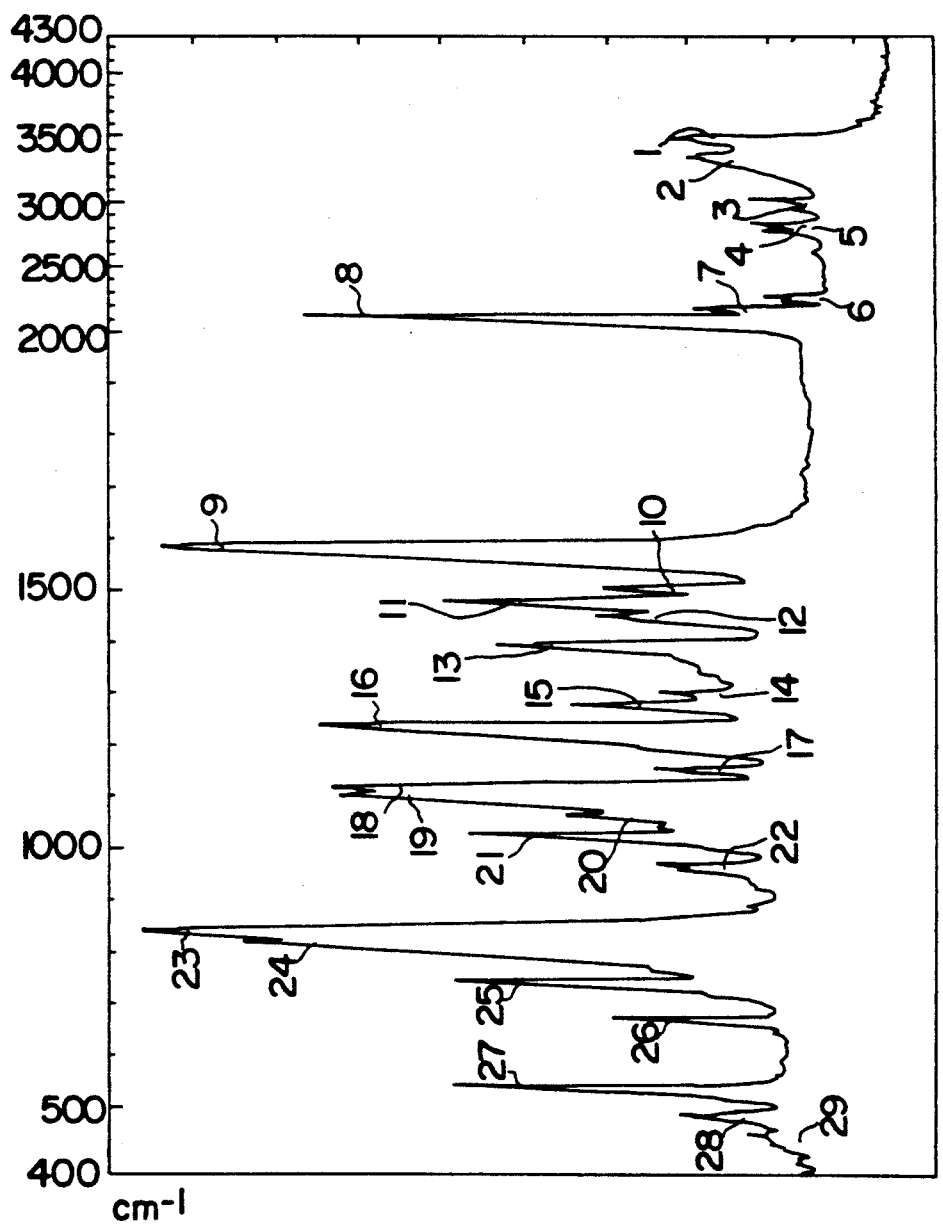
FIG. 9 is an infrared absorption spectrum of a compound of Formula (69).

(b) IR absorption spectrum
KBr tablets of diazo compounds (69) and (71) were prepared and measured for IR absorption spectrum. The results are shown in Table 10. The spectrum of compound (69) was shown in FIG. 9.

TABLE 10

(i) —N$_2^{\oplus}$ stretching frequency (cm$^{-1}$)

(69) 2234 (weak), 2162 (strong)
(71) 2240 (weak), 2158 (strong)

There has been reported that a compound in which BF$_4$, instead of PF$_6$ of Formula (71), is a counter-ion of diazonium, gives 2247 (weak) and 2165 (strong) (K. B. Whetsel, G. F. Hawkins, F. E. Johnson, J.Amer.Chem.Soc., 78, 3360(1956)).

(ii) Absorption spectra (cm$^{-1}$) which are present with a compound of Formula (69) but absent with a compound of Formula (71)

| | |
|---|---|
| 3570 (sharp) | stretching vibration of hydrogen bonded O—H |
| 3420 (broad) | |
| 1249 (sharp and strong) | antisymmetric stretch of |

-continued

| (ii) Absorption spectra (cm$^{-1}$) which are present with a compound of Formula (69) but absent with a compound of Formula (71) |
|---|
| —CH$_2$—OH—Ph |

The above values indicate that Formula (69) is correct. Analytical result of infrared absorption of Formula (69)

Peak table
Upper: 100.9  Lower: 13.3  Depth: 2.0

| No. | cm−1 | %T | No. | cm−1 | %T | No. | cm−1 | %T |
|---|---|---|---|---|---|---|---|---|
| 1 | 3578.0 | 73.7 | 2 | 3420.0 | 75.6 | 3 | 3124.0 | 82.4 |
| 4 | 2932.0 | 82.7 | 5 | 2874.0 | 83.9 | 6 | 2356.0 | 83.9 |
| 7 | 2234.0 | 76.6 | 8 | 2162.0 | 35.2 | 9 | 1591.0 | 19.9 |
| 10 | 1522.0 | 66.8 | 11 | 1493.0 | 49.7 | 12 | 1470.0 | 65.9 |
| 13 | 1410.0 | 55.0 | 14 | 1323.0 | 72.9 | 15 | 1296.0 | 63.1 |
| 16 | 1249.0 | 36.6 | 17 | 1176.0 | 72.3 | 18 | 1127.0 | 37.6 |
| 19 | 1112.0 | 38.6 | 20 | 1081.0 | 62.7 | 21 | 1040.0 | 52.3 |
| 22 | 992.0 | 72.4 | 23 | 845.0 | 17.7 | 24 | 824.0 | 28.8 |
| 25 | 760.0 | 51.0 | 26 | 694.0 | 67.6 | 27 | 557.0 | 50.5 |
| 28 | 511.0 | 75.0 | 29 | 476.0 | 82.1 | | | |

(c) UV absorption spectrum

Figure 10:
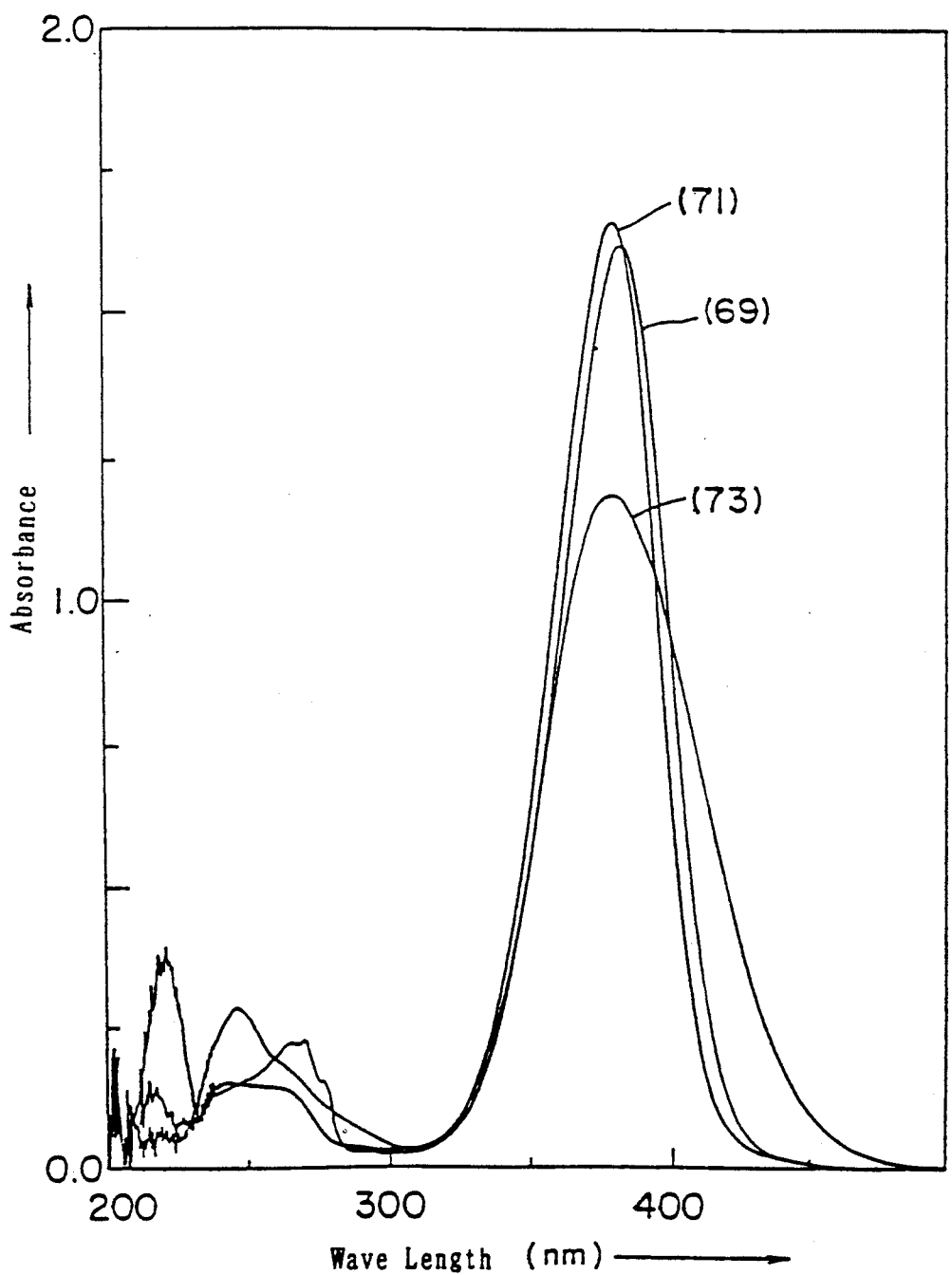
FIG. 10 shows ultraviolet absorption spectra of diazo compounds of Formulae (69), (71), and (73).

FIG. 10 shows UV absorption spectra of 2-methoxyethanol solutions which individually contain $4 \times 10^{-5}$ mole/l of diazo compounds (69), (71), and (73). Maximum absorption wavelength ($\mu$max), absorbance (A), and molar absorptivity ($\epsilon$) calculated from molecular weights of the individual compounds of Formulae (69), (71), and (73) are shown in Table 11.

TABLE 11

| | λmax (nm) | A | ε |
|---|---|---|---|
| Formula (69) | 382.5 | 1.63 | 40,750 |
| Formula (71) | 380.0 | 1.66 | 41,500 |
| Formula (73) | 379.0 | 1.21 | 30,250 |

The values of $\epsilon$ reported in the literature (Inoue, Kokado, Shimada, Nippon Kagaku Kaishi, Vol 12, p2272(1974)) of aqueous solutions of compounds in which Cl.1/2 ZnCl$_2$ is bonded in place of PF$_6$ of Formulae (71) and (73) are in good agreement with those values of $\epsilon$ of Formulae (71) and (73) of these experiments.

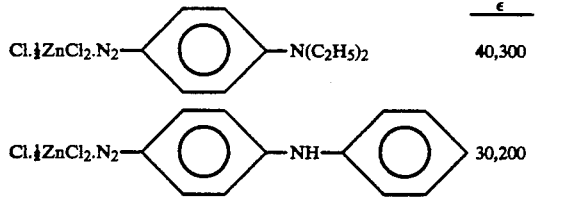

As described above in detail with reference to the examples, the present invention provides the following effects:

1) A multifunctional diazo compound, which can be handled under visible light free from ultraviolet, can be obtained.
2) A multifunctional diazo compound can be obtained, which has a large solubility in organic solvents, adequate as a photosensitive material for a lithographic printing plate, and can be easily developed with a developing solution mainly comprising an alkaline aqueous solution.
3) A multifunctional diazo compound can be obtained, which has a high solubility in water, appropriate for use as a photosensitive agent for a screen printing plate.
4) A multifunctional diazo compound, which has a high photosensitivity, can be obtained.
5) The present invention enables development of a multifunctional diazo compound which is simple for synthesis, and provides a low-cost production method thereof.

What is claimed is:

1. A photosensitive polyfunctional aromatic diazo compound selected from the group consisting of:

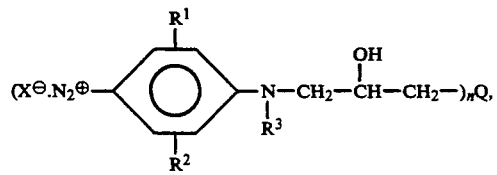

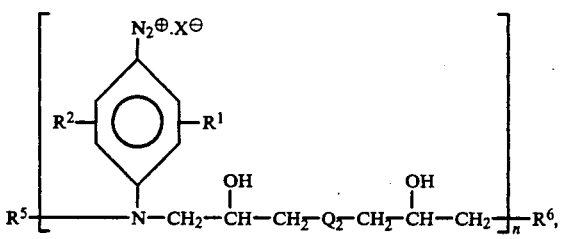

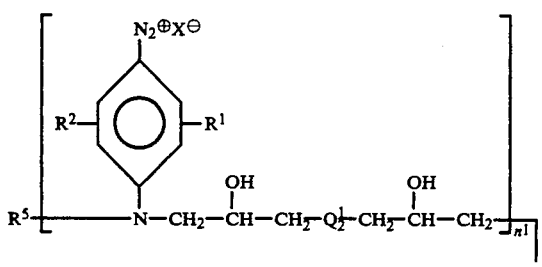

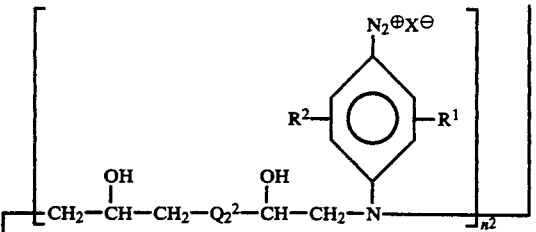

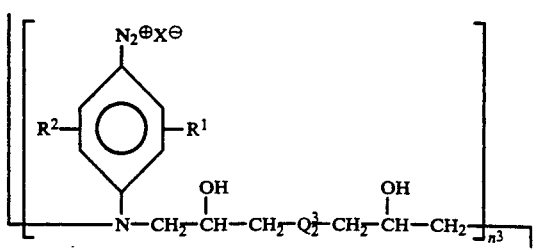

-continued

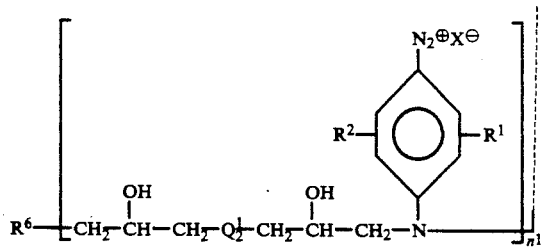

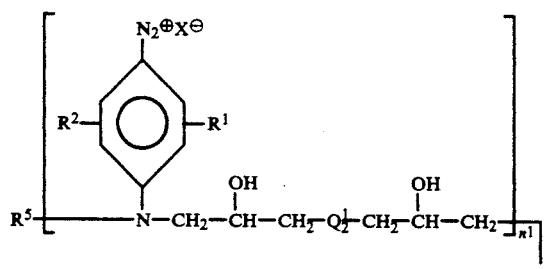

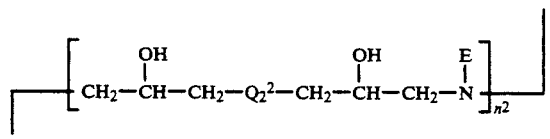

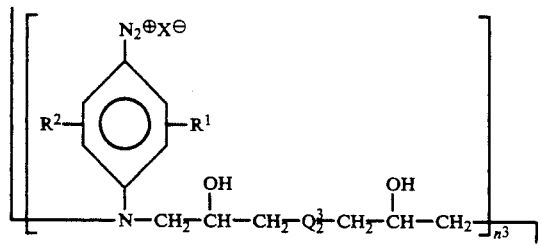

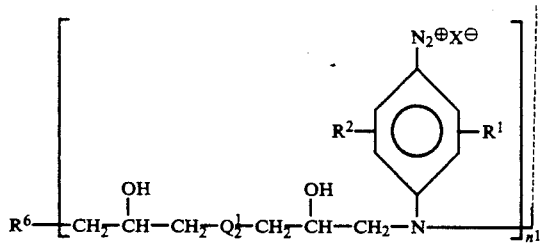

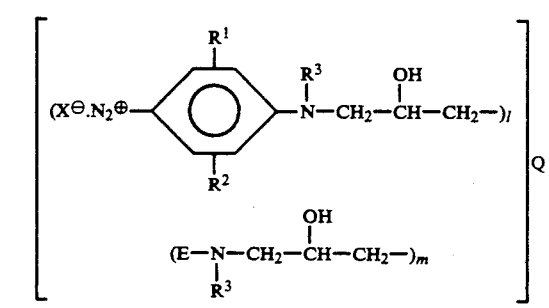

or
wherein $R^1$ and $R^2$ are selected from the group consisting of hydrogen, alkyl of 1 to 8 carbon atoms and alkoxy of 1 to 8 carbon atoms;

$R^3$ is selected from the group consisting of alkyl, aralkyl, chloro, bromo, hydroxy, alkoxy, aryloxy, aralkoxy, carboxy, sulfo, carbamoyl, sulfamoyl, substituted alkyl of 1 to 10 carbon atoms, substituted aralkyl of 7 to 20 carbon atoms, 2-(4-pyridyl)-ethyl, —CH₂CH(OH)CH₂Cl, —CH₂CH(OH)CH₂OH, —CH₂CH(OH)CH₂OR₄ and

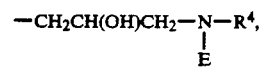

$R^4$ is selected from the group consisting of alkyl, aralkyl, aryl, alkylaryl, chloro, alkoxy, aryloxy, aralkoxy, carboxy, sulfo, carbamoyl, sulfamoyl-substituted alkyl, substituted aralkyl, aryl, alkylaryl, the alkyl having 1 to 10 carbon atoms and the aryl having 6 to 20 carbon atoms;

E is selected from the group consisting of alkyl, alkylphenyl, chloro, bromo, carboxy, sulfo, carbamoyl, sulfamoyl-substituted phenyl, and similarly substituted alkyl or alkylphenyl or phenylalkyl, the alkyl having 1 to 8 carbon atoms;

$X^-$ is an anion selected from the group consisting of chloride, bromide, sulfate, hydrogensulfate, phosphate, phosphite, tetrafluoroborate, hexafluorophosphate, chloride-zinc chloride, trifluoroacetate, oxalate, alkylsulfonate of 1 to 8 carbon atoms, trifluoromethane sulfonate, arylsulfonate of 6 to 24 carbon atoms, and 2-hydroxy-4-methoxybenzophenone-5-sulfonate;

Q is a residual group of the following polyhydroxy compounds or amino compounds from which n hydrogen atoms of hydroxyl groups or amino groups are removed:

polyhydroxy compounds selected from the group consisting of alkylene glycol of 2 to 8 carbon atoms, oxa-alkylene glycol of 4 to 9 carbon atoms, aralkylene glycol of 8 to 16 carbon atoms, glycerol, polyglycerol, trimethylolpropane, sorbitan, sorbitol, pentaerythritol, tris(2-hydroxyethyl)isocyanurate, hydroquinone, resorcinol, pyrogallol, phloroglucinol, bis(4-hydroxyphenyl)methane, 2,2-bis(4-hydroxyphenyl)propane, 2,2-bis(4-hydroxyphenyl)butane, bis(4-hydroxyphenyl)sulfone, 2,2-bis(3,5-dibromo-4-hydroxyphenyl)propane, bis(4-hydroxyphenyl)acetic acid, 2,2-bis(4-hydroxyphenyl)propionic acid, bis(3,5-dibromo-4-hydroxyphenyl)acetic acid, 2,2-bis(3,5-dibromo-4-hydroxyphenyl)propionic acid, 1,1,2,2,-tetra(4-hydroxyphenyl)ethane, phenol-formaldehyde-condensate, cresol-formaldehyde-condensate and polyhydroxy compounds formed by the condensation of each above-mentioned polyhydroxy compounds and epichlorohydrin, respectively;

amino compounds selected from the group consisting of alkylamine of 4 to 16 carbon atoms, aralkylamine of 7 to 14 carbon atoms, arylamine of 6 to 14 carbon atoms, alkyarylamine of 7 to 20 carbon atoms, chloro, bromo, carboxy, sulfo, carbamoyl, sulfamoyl substituted compounds of the above-mentioned four groups of amines, diethylenetriamine, triethylenetetramine, ethyleneurea, isocyanuric acid, aniline-formaldehyde-condensate, toluidine-formaldehyde-condensate, and amino compounds formed by the condensation of each above-mentioned amino compounds and epichlorohydrin, respectively;

Q₂ is a divalent group derived from the following diols or amines from which two hydrogen atoms of hydroxyl groups or amino groups are removed:

diols selected from the group consisting of alkylene glycol of 2 to 8 carbon atoms, oxaalkylene glycol of 4 to 9 carbon atoms, aralkylene glycol of 8 to 16 carbon atoms, hydroquinone, resorcinol, bis(4-hydroxyphenyl)methane, 2,2-bis(4-hydroxyphenyl)propane, 2,2-bis(4-hydroxyphenyl) butane, bis(4-hydroxyphenyl)sulfone, 2,2-bis(3,5-dibromo-4-hydroxyphenyl)propane, bis(4-hydroxyphenyl)acetic acid, 2,2-bis(4-hydroxyphenyl)propionic acid, bis(3,5-dibromo-4-hydroxyphenyl)acetic acid, 2,2-bis(3,5-dibromo-4-hydroxyphenyl)propionic acid, and diols formed by the condensation of each above-mentioned diols and epichlorohydrin, respectively;

amino compounds selected from the group consisting of alkylamine of 4 to 16 carbon atoms, aralkylamine of 7 to 14 carbon atoms, arylamine of 6 to 14 carbon atoms, alkylarylamine of 7 to 20 carbon atoms, chloro, bromo, carboxy, sulfo, carbamoyl, sulfamoyl-substituted compounds of the above-mentioned four groups of amines, and amino compounds formed by the condensation of each above-mentioned amines and epichlorohydrin, respectively;

Q2¹ to Q2¹ are divalent groups of at least two different types of Q2;

R⁵ is selected from the group consisting of

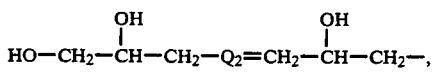

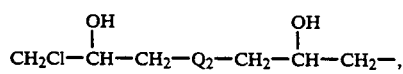

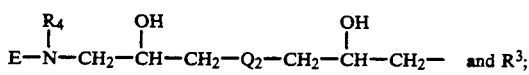

R¹ is selected from the group consisting of

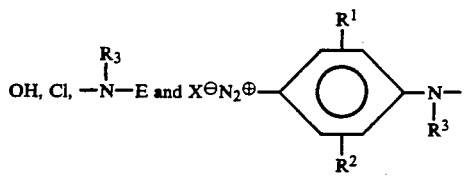

n is an integer from 2 to 20; n¹ to n^i is an integer from 0 to 4 and n¹+n²+n³+ ... +ni=2 to 20; is an integer from 1 to 15, m is an integer from 1 to 15.

2. A photosensitive composition comprising a photosensitive polyfunctional aromatic diazo compound of claim 1, an oleophilic resinous substance suitable for a binder comprising at least a high molecular weight organic compound containing aliphatic or aromatic hydroxyl group, and carboxyl or sulfo or carbamoyl or sulfonamide group as necessary, at least one additive selected from the group consisting of a dye, a surface active agent a plasticizer, and an oleophilic compound, and a stabilizer; said composition being coated on a base material selected from the group consisting of an aluminum plate, a sheet of paper, a plastic film, a glass plate, and a screen mesh comprising a synthetic resin or stainless steel.

3. The photosensitive composition of claim 2 suitable for a presensitized lithographic plate wherein said base material is a grained and anodized aluminum plate, and said binder is selected from the group consisting of cresol resin, polyester, polyamide, polyurethane, polyvinyl chloride, polymethyl methacrylate, polystyene, polyvinyl acetate, and copolymers of vinyl compounds selected from the group consisting of alkyl acrylates, alkyl methacrylates, acrylic acid, methacrylic acid, crotonic acid, maleic acid, 2-hydroxyethyl acrylate, 2-hydroxyethyl methacrylate, glycerol-monoacrylate, glycerol-monomethacrylate, N-(4-hydroxyphenyl)methacrylamide, N-(4-hydroxyphenyl)acrylamide, N-(4-sulfamoylphenyl)methacrylamide, N-(4-sulfamoylphenyl)acrylamide, hydroxyphenyl acrylates, hydroxyphenyl methacrylates, hydroxystyrenes, acrylonitrile, methacrylonitrile, N-alkyl acrylamides, N-alkyl methacrylamides, N-vinylpyrrolidone, 4-vinylpyridine, vinyl ethers, and styrenes.

4. The photosensitive composition of claim 2 suitable for a presensitized screen printing plate wherein said base material is a screen mesh comprising a synthetic resin or stainless steel; and said binder is selected from the group consisting of polyvinyl alcohol, polyvinyl alcohol with pendant styrylpyridinium groups, polyvinyl acetate, gelatin, casein, glue, carboxymethyl cellulose, polyacrylamide, polyvinylpyrrolidone, and polymethacrylic acid.

5. The photosensitive composition of claim 2 suitable for a presensitized colored image formation material wherein said base material is a glass plate or a film or plate comprising polyethylene terephthalate, polypropylene, polystyrene, polycarbonate, polyvinyl chloride, or cellulose triacetate; and said binder is selected from the group consisting of polyvinyl alcohol, gelatin, casein, glue, carboxymethyl cellulose, polyacrylamide, polyvinylpyrrolidone, and polymethacrylic acid and its salts; and further comprising a coloring agent selected from water-dispersible pigments, and water-soluble or alcohol-soluble dyes.

* * * * *